United States Patent
Iftekhar et al.

(10) Patent No.: US 11,717,392 B2
(45) Date of Patent: Aug. 8, 2023

(54) MODULATION OF INFLAMMATORY RESPONSE FOLLOWING ENDOVASCULAR TREATMENT

(71) Applicant: Endologix LLC, Irvine, CA (US)

(72) Inventors: Mohammed Arif Iftekhar, Irvine, CA (US); Peter Costandi, Irvine, CA (US); Carlos Ortega, Irvine, CA (US); Chris Williams, Irvine, CA (US); Craig Welk, Irvine, CA (US)

(73) Assignee: Endologix LLC, Irvine, CA (US)

( * ) Notice: Subject to any disclaimer, the term of this patent is extended or adjusted under 35 U.S.C. 154(b) by 0 days.

(21) Appl. No.: 17/049,932

(22) PCT Filed: Apr. 22, 2019

(86) PCT No.: PCT/US2019/028538
§ 371 (c)(1),
(2) Date: Oct. 22, 2020

(87) PCT Pub. No.: WO2019/209731
PCT Pub. Date: Oct. 31, 2019

(65) Prior Publication Data

US 2021/0093440 A1 Apr. 1, 2021

Related U.S. Application Data

(60) Provisional application No. 62/661,569, filed on Apr. 23, 2018.

(51) Int. Cl.
*A61F 2/07* (2013.01)
*A61F 2/958* (2013.01)

(52) U.S. Cl.
CPC ............... *A61F 2/07* (2013.01); *A61F 2/958* (2013.01); *A61F 2002/077* (2013.01); *A61F 2210/0085* (2013.01)

(58) Field of Classification Search
CPC ...... A61F 2/07; A61F 2/958; A61F 2002/077; A61F 2210/0085; A61F 2210/008;
(Continued)

(56) References Cited

U.S. PATENT DOCUMENTS 5,330,528 A * 7/1994 Lazim ................ A61F 2/07
623/1.25
5,951,599 A * 9/1999 McCrory ............ A61F 2/07
623/1.1
(Continued)

FOREIGN PATENT DOCUMENTS

JP 2008-539050 A 11/2008
WO WO-2004026183 A2 * 4/2004 ............ A61F 2/07
(Continued)

OTHER PUBLICATIONS

International Search Report and Written Opinion dated Jul. 8, 2019, from application No. PCT/US2019/28538.
(Continued)

*Primary Examiner* — Paul B Prebilic
(74) *Attorney, Agent, or Firm* — Foley & Lardner LLP

(57) ABSTRACT

A method of treating an aortic aneurysm of a patient with an endovascular graft system and mitigating post implant syndrome associated therewith comprises placing at least one prosthesis across an aneurysmal space. The prosthesis comprises a double-walled filling structure and a stent-graft. The stent graft is radially expanded at a first pressure and the filing structure is filled with a first filing agent to contact a thrombus in the aortic aneurysmal space. After the first filling agent is removed, the filling structure is filled with a second filling agent to contact the thrombus. Next the stent-graft is expanded at a second pressure causing the filing structure to place an effective amount of pressure on
(Continued)

the thrombus and substantially mitigating the effects of post implant syndrome associated with the prosthesis.

22 Claims, 11 Drawing Sheets

(58) Field of Classification Search
CPC ........ A61F 2220/0008; A61F 2250/001; A61F 2250/0009; A61F 2250/0013; A61F 2250/0039; A61F 2250/0069; A61F 2250/0067
See application file for complete search history.

(56) References Cited

U.S. PATENT DOCUMENTS

| | | | |
|---|---|---|---|
| 8,048,145 B2 * | 11/2011 | Evans | A61F 2/07 623/1.25 |
| 8,801,768 B2 * | 8/2014 | Karwa | A61B 17/12118 623/1.11 |
| 8,945,199 B2 | 2/2015 | Ganpath et al. | |
| 9,724,186 B2 | 8/2017 | Chobotov | |
| 11,497,597 B2 * | 11/2022 | Schreck | A61B 17/12118 |
| 2003/0036745 A1 | 2/2003 | Khosravi et al. | |
| 2010/0036360 A1 | 2/2010 | Herbowy et al. | |
| 2014/0277331 A1 | 9/2014 | Ngo et al. | |
| 2016/0367352 A1 | 12/2016 | Heiss | |
| 2017/0239035 A1 | 8/2017 | Schreck et al. | |
| 2017/0290654 A1 | 10/2017 | Sethna | |

FOREIGN PATENT DOCUMENTS

| | | | |
|---|---|---|---|
| WO | WO-2006/116725 A2 | 11/2006 | |
| WO | WO-2016109757 A1 * | 7/2016 | ....... A61B 17/12113 |

OTHER PUBLICATIONS

Extended European Search Report dated Jan. 18, 2022, from application No. 19792104.2.
International Preliminary Report on Patentability dated Nov. 5, 2020, from application No. PCT/US2019/028538.
Japanese Office Action dated May 9, 2023, for application No. 2020-560309.

* cited by examiner

MODULATION OF INFLAMMATORY RESPONSE FOLLOWING ENDOVASCULAR TREATMENT

CROSS-REFERENCE TO RELATED PATENT APPLICATIONS

This application is a U.S. National Stage Application under 35 U.S.C. § 371 of International Application No. PCT/US2019/028538, filed Apr. 22, 2019, which claims priority from U.S. Provisional Patent App. Ser. No. 62/661,569, filed Apr. 23, 2018, the entire contents of each of which are incorporated by reference herein.

TECHNICAL FIELD

The present technology relates generally to endoluminal vascular prostheses and methods of placing such prostheses. More particularly, various embodiments relate to endoluminal vascular prostheses and methods of placing such prostheses for treating aortic aneurysms.

BACKGROUND

The following description of the background is provided simply as an aid for understanding without any admission that it describes or constitutes prior art.

Aneurysms are enlargements or bulges in blood vessels that are often prone to rupture and which therefore present a serious risk to a patient. Aneurysms may occur in any blood vessel but are of particular concern when they occur in the cerebral vasculature or the patient's aorta.

Abdominal aortic aneurysms (AAA's) are classified based on their location within the aorta as well as their shape and complexity. Aneurysms that are found below the renal arteries are referred to as infrarenal abdominal aortic aneurysms. Suprarenal abdominal aortic aneurysms occur above the renal arteries. Thoracic aortic aneurysms (TAA's) occur in the ascending, transverse, or descending part of the upper aorta. Infrarenal aneurysms are the most common, representing about 70% of all aortic aneurysms. Suprarenal aneurysms are less common, representing about 20% of the aortic aneurysms. Thoracic aortic aneurysms are the least common and often the most difficult to treat.

The most common form of aneurysm is "fusiform," where the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. A common treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Endoluminal grafts have come into widespread use for the treatment of aortic aneurysms in patients. A typical endograft procedure utilizes a stent graft placement to treat the aneurysm. The purpose of the graft is generally to isolate the diseased portion of the aortic wall from the aortic blood pressure and prevent further dilatation or rupture of the diseased portion of the aortic wall. In general, endoluminal repairs access the aneurysm "endoluminally" through either or both common iliac arteries. The grafts are then implanted. Successful endoluminal procedures have a much shorter recovery period than open surgical procedures.

It is desirable, therefore, to improve the design and use of endoluminal grafts.

SUMMARY OF THE DISCLOSURE

The present disclosure provides improved methods, systems and devices for treatment of aneurysms, including aortic aneurysms. Various embodiments allow for reducing acute and/or chronic post-implantation inflammatory responses, among other things, upon deployment of endovascular graft systems. Chronic inflammatory responses can potentially lead to major adverse events such as major adverse cardiac events (MACE), acute renal failure, readmission, and even death. Various embodiments provide improved compositions, systems, and methods of placing such systems that will modulate and minimize acute as well as chronic inflammation post-implantation. Accordingly, in the exemplary embodiments, a method is provided for treating an aortic aneurysm of a patient using an endovascular graft system which mitigates post implant syndrome associated with the treatment. The method includes placing at least one prosthesis in the aortic aneurysmal space, the prosthesis including a stent-graft and a double-walled filling structure. The filling structure includes an outer wall, an inner wall, and a fillable space between the outer wall and the inner wall. As described in further detail below, the system may include a plurality of filling structures and stent-grafts. Moreover, the order placement and deployment (including expansion and filling) may vary. Following placement of the stent-graft across the aneurysm, it is radially expanded at a first pressure with an expanding structure such as an expansion balloon. The filling structure is then filled with a first filling agent such that the filling structure expands and contacts a thrombus disposed in the aneurysmal space. Once the first filling agent is removed, the filling structure is then filled with a second filling agent such that the filling structure expands and contacts the thrombus again. Next, the stent-graft is radially inflated with an expansion balloon at a second pressure, with the second pressure being greater than the first pressure, which causes the filling structure with the second filling agent to place an effective amount of pressure on the thrombus. Generally, the effective amount of pressure placed on the thrombus can substantially mitigate the effects of post implant syndrome associated with the prosthesis such as inflammatory response. The mechanisms potentially contributing to the mitigation of inflammation are further described in detail below and include space filling, perfusion elimination, acute pressurization and chronic pressurization.

Another exemplary embodiment that is a method of treating an aortic aneurysm in a blood vessel of a patient in need thereof with an endovascular graft system includes exerting an effective amount of pressure on an intraluminal thrombus or a vessel wall of a segment of the blood vessel to be treated to displace biological fluid from the thrombus or the vessel wall, thereby reducing an inflammatory response associated with the treatment.

Another exemplary method of treating an aortic aneurysm in a blood vessel of a patient in need thereof with an endovascular graft system includes preventing new thrombus formation in a segment of the blood vessel to be treated, thereby reducing an inflammatory response associated with the treatment.

Another exemplary method of treating an aortic aneurysm in a blood vessel of a patient in need thereof with an endovascular graft system includes blocking access of an intraluminal thrombus in a segment of the blood vessel to be treated to circulating blood, thereby reducing an inflammatory response associated with the treatment.

Yet another method of treating an aortic aneurysm in a blood vessel of a patient in need thereof with an endovascular graft system includes filling a space in the aneurysm around the endovascular graft system with a fluid or polymer, thereby reducing an inflammatory response associated with the treatment.

In still another example, a method of reducing an inflammatory response in a patient undergoing endovascular graft system implantation for treating an aortic aneurysm includes exerting an effective amount of pressure on an intraluminal thrombus or a vessel wall of a segment of a blood vessel to be treated to displace fluid from the thrombus or the vessel wall, thereby reducing the inflammatory response associated with the implantation.

BRIEF DESCRIPTION OF THE DRAWINGS

These and other features, aspects and advantages of the present disclosure will now be described in connection with non-exclusive embodiments, in reference to the accompanying drawings. The illustrated embodiments, however, are merely examples and are not intended to limit the invention. The following are brief descriptions of the drawings, which may not be drawn to scale.

DETAILED DESCRIPTION

Figure 1:
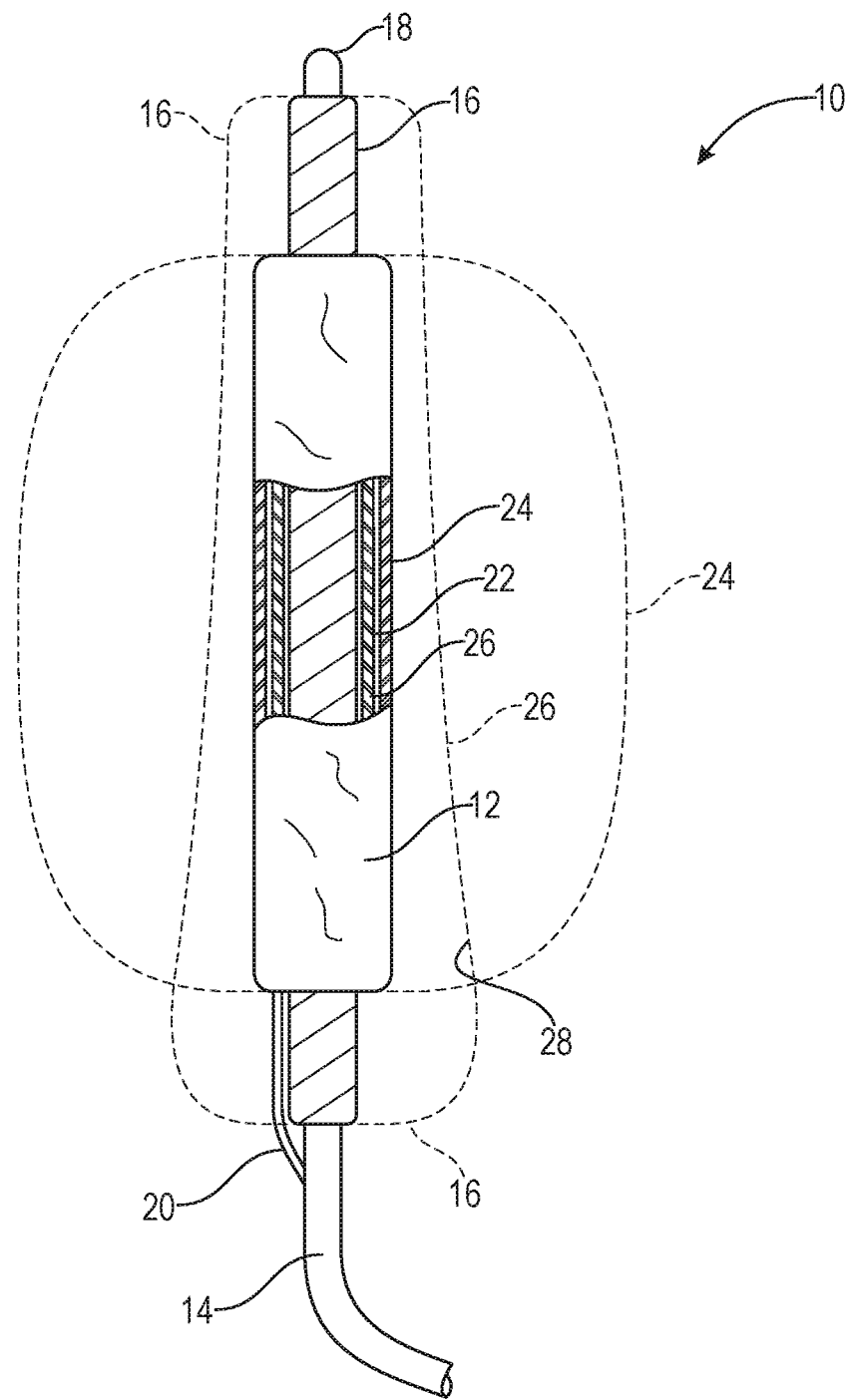
FIG. 1 illustrates a prosthesis system including a filling structure mounted over a delivery catheter.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and may be practiced with any other embodiment(s).

In practicing the present methods, many techniques in molecular biology, protein biochemistry, cell biology, microbiology and recombinant DNA are used. See, e.g., Sambrook and Russell eds. (2001) "Molecular Cloning: A Laboratory Manual," 3rd edition; the series Ausubel et al. eds. (2007) "Current Protocols in Molecular Biology"; the series "Methods in Enzymology" (Academic Press, Inc., N.Y.); MacPherson et al. (1991) "PCR 1: A Practical Approach" (IRL Press at Oxford University Press); MacPherson et al. (1995) "PCR 2: A Practical Approach"; Harlow and Lane eds. (1999) "Antibodies, A Laboratory Manual"; Freshney (2005) "Culture of Animal Cells: A Manual of Basic Technique," 5th edition; Gait ed. (1984) "Oligonucleotide Synthesis"; U.S. Pat. No. 4,683,195; Hames and Higgins eds. (1984) "Nucleic Acid Hybridization"; Anderson (1999) "Nucleic Acid Hybridization"; Hames and Higgins eds. (1984) "Transcription and Translation"; "Immobilized Cells and Enzymes" (IRL Press (1986)); Perbal (1984) "A Practical Guide to Molecular Cloning"; Miller and Calos eds. (1987) "Gene Transfer Vectors for Mammalian Cells" (Cold Spring Harbor Laboratory); Makrides ed. (2003) "Gene Transfer and Expression in Mammalian Cells"; Mayer and Walker eds. (1987) "Immunochemical Methods in Cell and Molecular Biology" (Academic Press, London); and Herzenberg et al. eds (1996) "Weir's Handbook of Experimental Immunology."

General Overview

As the prevalence of stent graft based endo-prostheses for the treatment of infrarenal aortic aneurysms increased in the late 1990s, early experience was focused on the morbidity and mortality benefits of this less invasive alternative to open surgical repair. Of note was an acute inflammatory response experienced by some patients, later termed Post Implantation Syndrome (PIS). Velazquez et al., Amer J Surg. 178:185-9 (1999) described such a syndrome where pyrexia and leukocytosis were observed in the days following endovascular aortic repair (EVAR). In their retrospective analysis of 12 elective cases, 67% experienced a high grade fever exceeding 38.6° C. ($p<0.05$) while 58% experienced a proliferation of white blood cells in excess of 11,000 cells/ $\mu$L ($p<0.05$), and sepsis evaluations identified no source of infection in a majority of patients (97%). These results suggested that PIS may be related to a local inflammatory reaction, possibly part of the healing response following EVAR.

To substantiate the observational outcomes in these patients, several authors aimed to identify a more mechanistic description of the underlying pathophysiology.

Arnaoutoglou at el. J Vac Surg. 63:1248-55 (2016) conducted a prospective study of 182 patients monitoring not only for downstream pyrexia and leukocytosis, but also for specific inflammatory markers (high sensitivity C-reactive protein [hs-CRP] & Interleukin-6 [IL-6]) and notable adverse events (major adverse cardiac event [MACE], acute renal failure, readmission and death from any cause) extending beyond the post implant time point. Consistent with their predecessors, they defined PIS as persistent fever in excess of 38° C. lasting for longer than 1 day and a white blood cell count (WBC) of greater than 12,000 cells/µL with negative blood cultures. They noted PIS in 35.7% of patients. WBC, hs-CRP and IL-6 were all statistically elevated in the PIS group vs the non-PIS group ($p<0.001$) in the first postoperative month, with further granularity suggesting that grafts made of polyester were more prone to PIS development than those made of expanded polytetrafluoroethylene (ePTFE). Though hs-CRP and IL-6 levels were attenuated back to normal levels at the one-year follow-up, WBC remained elevated ($p<0.05$). With respect to morbidity and mortality, the authors found that patients diagnosed with PIS were about 4.5 times more likely to suffer a MACE ($p=0.007$) and 4.51 times more likely to suffer a non-cardiac adverse event ($p=0.005$) than non-PIS patients, concluding statistically that the inflammatory syndrome was the only independent predictor of adverse outcomes. These results corroborated the clinical phenomenon of PIS, relating it to the upregulation of pro-inflammatory kinetics with association to severe adverse events.

The advent of endovascular aneurysm sealing (EVAS) as an alternative to EVAR introduces the possibility of modulating any ensuing inflammatory response. With EVAR, the stent graft forms a cylindrical conduit within the existing blood flow lumen and, in general, the outer diameter of the stent graft will not fill the entire cross section of the flow lumen, but rather allow for space between the border of the device and existing thrombus. This space will most likely be pervaded by the formation of fresh thrombus, potentially exacerbating an inflammatory response that has been associated with thrombotic activity (Roumen-Klappe et al., J Vas Surg. 35(4):701-6 (2002)). By contrast, EVAS aims to occupy the non-flow lumen space outside of the graft conduit with polymer, preventing further thrombus formation. This fundamental difference between techniques may provide an opportunity for EVAS to have a beneficial effect with respect to thrombus formation, and consequently, the development of PIS.

Berg et al., J End Ther. 24(5):67-4 (2017) investigated this difference in PIS between EVAR and EVAS. The authors analyzed retrospective single center data of 63 EVAR and 41 EVAS patients through 30 days for the prevalence of PIS, inflammatory markers, and clinical complications as in previous reports but with the added variable of aneurysm treatment type. As a second layer of analysis, they conducted a propensity score-matched analysis, where a pairing algorithm was used to adjust for treatment selection bias and possible imbalances in baseline patient characteristics between groups. PIS was noted in 5.1% of EVAS patients versus 20.5% with EVAR. Pyrexia (maximum temperature>38° C., WBC (>12,000 cells/µL), and hs-CRP were all diminished in EVAS versus EVAR ($p=0.05$, $p=0.003$ and $p<0.001$, respectively). In the propensity score-matched subset (39 patients in each group), serious adverse events (i.e. cardiac decompensation, secondary intervention for type I endoleak, and angina pectoris with elevated troponin levels) and endoleaks through 30 days were less frequent with EVAS, but the proportions were not significantly different. They also concluded that the choice of EVAR graft material influenced postoperative and 30 day clinical outcomes, with greater overall risk observed with polyester grafts.

The present technology is based, in part, on new insights into the pathway(s) by which EVAS may diminish an inflammatory response and yield an all-cause mortality benefit relative to EVAR. Based in part on the discovery of novel mechanisms of action of EVAS, in one aspect, the present technology describes systems and methods for modulating acute and chronic inflammatory responses after implantation and of endovascular grafts.

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "an agent" includes a combination of two or more agents, and the like. Generally, the nomenclature used herein and the laboratory procedures in cell culture, molecular genetics, organic chemistry, analytical chemistry and nucleic acid chemistry and hybridization described below are those well-known and commonly employed in the art. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term. As used herein, the terms "about" and "substantially" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, through the endovascular graft delivery system, orally, intranasally, parenterally (intravenously, intramuscularly, intraperitoneally, or subcutaneously), rectally, intrathecally, or topically. Administration includes self-administration and the administration by another.

As used herein, the term "and/or" includes any and all combinations of one or more of the associated listed items.

As used herein, the term "effective amount" refers to a quantity sufficient to achieve a desired therapeutic and/or prophylactic effect. Thus, an effective amount of pressure can refer to pressure which results in the displacement of fluids from a biological tissue. This includes, but is not limited to, displacement of fluids and/or pro-inflammatory agents or molecules from the thrombus or aneurysm tissue which results in the prevention of, or a decrease in an inflammatory response. The amount of pressure applied to achieve the desired effects can depend on the location, degree, and type of the aneurysm, and on the individual patient. Moreover, an effective amount of pressure may also refer to pressure which results in biological remodeling of the thrombus or aneurysmal tissue. The remodeling may include building or blocking fluid pathways including vasculature. Furthermore, an effective amount of pressure may quantitatively refer to specific pressure values or pressure ranges (considering duration as well) as further elaborated the present disclosure.

As used herein, the terms "individual", "patient", or "subject" can be an individual organism, a vertebrate, a mammal, or a human. In some embodiments, the individual, patient or subject is a human.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences (20$^{th}$ edition, ed. A. Gennaro, 2000, Lippincott, Williams & Wilkins, Philadelphia, Pa.).

As used herein, the term "therapeutic agent" is intended to mean a compound that, when present in an effective amount, produces a desired therapeutic effect on a subject in need thereof.

"Treating" or "treatment" as used herein covers the treatment of a disease or condition described herein, in a subject, such as a human, and includes: (i) inhibiting a disease or condition, i.e., arresting its development; (ii) relieving a disease or condition, i.e., causing regression of the disorder; (iii) slowing progression of the disease or condition; and/or (iv) inhibiting, relieving, or slowing progression of one or more symptoms of the disease or condition. In some embodiments, treatment means that the symptoms associated with the disease or condition are, e.g., alleviated, reduced, cured, or placed in a state of remission.

It is also to be appreciated that the various modes of treatment of diseases or conditions as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition. The treatment may also refer to a surgical procedure or to the placement of a prosthesis (e.g., an endovascular graft system) to treat a disease or condition.

Methods of Modulating Inflammation
Post-Implantation

EVAS has been shown to be potentially associated with a blunted systemic inflammatory response compared with EVAR in the 30-day period following post-implantation (Berg et al., J End Ther. 24(5):67-4 (2017)). Berg et al. failed to demonstrate a statistically significant difference between EVAS and EVAR in terms of major cardiac or non-cardiac related adverse events. However, in a non-score matching analysis where all EVAS and EVAR patients were included, EVAS showed a significant difference in incidence of major adverse cardiac events (p=0.04) (data not shown). Without being bound by theory, based on new insights into the pathway(s) by which EVAS may diminish an inflammatory response, the present technology is directed to methods and systems of aneurysm repair that modulate and minimize both acute and chronic inflammation post-implantation of the endovascular graft system. Based on the correlation between inflammation and cardiovascular risk (Willerson et al., Circulation 109[suppl II]: II-2-II-10 (2004)), and the correlation between PIS and associated inflammatory markers to adverse events, the reduction in inflammation further translates to a reduction in the incidence of major cardiovascular as well as non-cardiovascular adverse events. The present technology is based, in part, on the discovery of several mechanisms of action by which both acute as well chronic inflammation associated with the implantation of an endovascular graft system (e.g., to treat an aortic aneurysm including both abdominal aortic aneurysms (AAA's) and thoracic aortic aneurysms (TAA's)) can be mitigated. However, it is noted that the present technology is contemplated for many forms of aneurysms including thoracic, abdominal, infrarenal, juxtarenal, pararenal or paravisceral or a combination thereof.

A. Space-Filling Mechanism

Figure 5A:
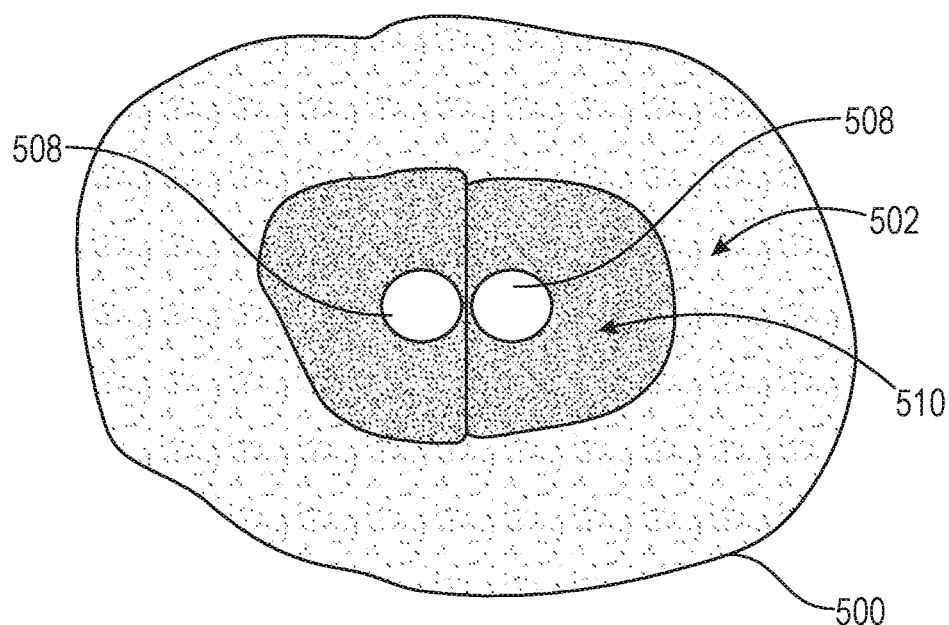
FIGS. 5A and 5B depict the reduction of formation of new-onset thrombus by filling the flow lumen of an aneurysmal space with a filling agent in an endovascular aneurysm sealing (EVAS) system as compared to an endovascular aortic repair (EVAR) system.
Figure 5B:
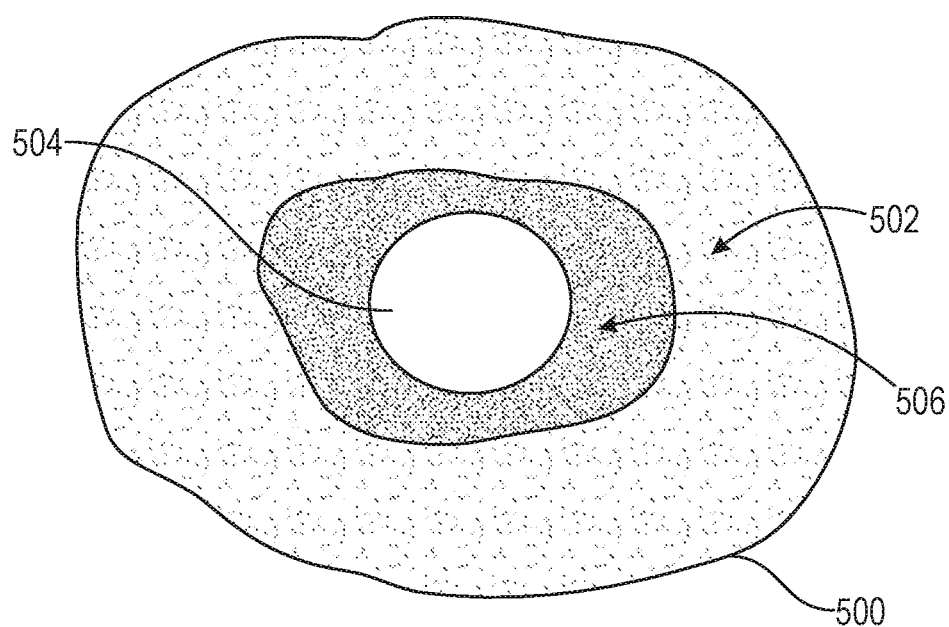

Studies have substantiated the correlation between PIS and associated inflammatory markers to adverse outcomes. Thrombus is proposed herein to be the mediator of this relationship. Both mature thrombus within the aneurysmal sac and newly formed thrombus following treatment, may provide a milieu for pro-inflammatory cytokines and other agents and facilitate their cell signaling pathways. With some level of communication with the circulatory system through patent blood vessels and capillaries that permeate through such thrombus formations, access to the central circulatory system is possible. A causal link is then possible that implicates thrombus as the mediator of an inflammatory response, resulting in long term morbidity and mortality. The unique property of EVAS of reducing the volume of new deposits compared to EVAR may be consequential for modulating the inflammatory response post-implantation (FIGS. 5A and 5B). Accordingly, in one aspect, the present technology is directed to methods and systems for the endoluminal treatment of aneurysms, particularly aortic aneurysms including both abdominal aortic aneurysms (AAA's) and thoracic aortic aneurysms (TAA's), including preventing new thrombus formation in the segment of the blood vessel to be treated, thereby reducing the inflammatory response associated with the treatment.

In some embodiments, the present technology is directed to systems and methods of treating an aneurysm including permanently filling the patent aneurysmal space with a filling agent (e.g., a gas, a fluid, a polymer, or a combination thereof) such that the filling agent completely or partially displaces existing thrombus and/or prevents formation of new thrombus. This reduction in the thrombus volume may reduce the overall level of pro-inflammatory molecules (e.g., pro-inflammatory cytokines such as but not limited to tumor necrosis factor alpha (TNF-α) or cyclophilin A, and angiotensin II; and reactive oxygen and nitrogen species (ROS/RNS)). In some embodiments, the filling agent is a curable polymer, which after curing, will have a fixed shape. The polymers may be delivered as liquids, gels, foams, slurries, or the like. In some embodiments, the polymers may be epoxies or other curable two-part systems. In some embodiments, the polymer may comprise a single material which when exposed to the vascular environment changes state over time, typically from zero to ten minutes. In some embodiments, the filling agent is saline. In some embodiments, the filling agent is present within one or more filling structures that form a part of the endovascular graft system. In some embodiments, the filling structure is a double-walled filling structure and the filling agent is injected into the internal space between the outer wall and the inner wall, such that the outer wall conforms to the shape of the aneurysm. The double-walled filling structures are pre-shaped and otherwise adapted to substantially fill the enlarged volume of an aneurysm when filled, particularly a fusiform aneurysm, leaving a lumen in place for blood flow. In some embodiments, the outer wall of the double-walled filling structure is degradable and degrades within the body over a period of time, leaving behind, for example, a hardened or cured polymer filling. In some embodiments, the filling agent (e.g., fluid, polymer, or a combination thereof) is injected directly into the patent aneurysmal space and surrounds the endovascular graft system. Injecting the filling agent directly into the patent aneurysmal space provides the ability to apply pressure directly to the thrombus or wall of the segment of the blood vessel being treated, further aiding in the displacement of pro-inflammatory molecules from the treatment site.

B. Elimination of Perfusion

Figure 6:
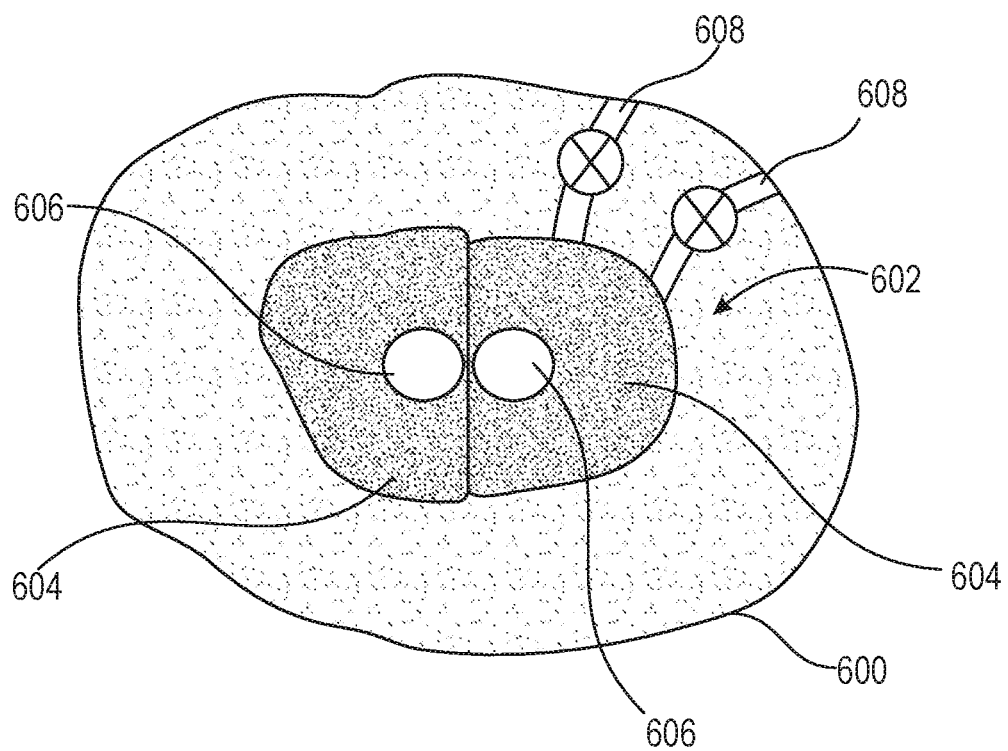
FIG. 6 depicts the prevention or elimination of perfusion to a thrombus and consequent decrease in communication of pro-inflammatory agents from the thrombus into the general circulation.

EVAS technology has been shown to reduce the incidence of type II endoleaks as compared to EVAR (Thompson et al., J EndoVasc Ther. 23(5):685-692 (2016)). The ability to fill the aneurysmal space with polymer may prevent the communication between entry and exit lumbar vessels that are required to sustain an endoleak (FIG. 6). Without being bound by theory, preventing the access of mature thrombus to circulating blood by sealing patent vessels through sac filling may further reduce or eliminate the cell signaling pathways of pro-inflammatory molecules present in biologically active thrombus. This may effectively blunt the ability of thrombus to mediate PIS as well as chronic inflammation. Accordingly, in one aspect, the present technology is directed to methods and systems for the endoluminal treatment of aneurysms, particularly aortic aneurysms including both abdominal aortic aneurysms (AAA's) and thoracic aortic aneurysms (TAA's), including blocking the access of the intraluminal thrombus in the segment of the blood vessel to be treated to circulating blood, thereby reducing the inflammatory response associated with the treatment.

In some embodiments, the present technology is directed to systems and methods of treating an aneurysm that comprise filling the patent aneurysmal space with a filling agent (e.g., a gas, a fluid, a polymer, or a combination thereof) such that the filling agent reduces or eliminates perfusion to thrombus and consequently reduces or eliminates release of pro-inflammatory molecules from thrombus into circulation. This reduction or elimination of perfusion to thrombus volume may reduce the communication of pro-inflammatory molecules (e.g., pro-inflammatory cytokines such as but not limited to tumor necrosis factor alpha (TNF-α) or cyclophilin A, and angiotensin II; and reactive oxygen and nitrogen species (ROS/RNS)) into the general circulation. In some embodiments, the filling agent is a curable polymer, which after curing, will have a fixed shape. The polymers may be delivered as liquids, gels, foams, slurries, or the like. In some embodiments, the polymers may be epoxies or other curable two-part systems. In some embodiments, the polymer may comprise a single material which when exposed to the vascular environment changes state over time, typically from zero to ten minutes. In some embodiments, the filling agent is saline. In some embodiments, the filling agent is present within one or more filling structures that form a part of the endovascular graft system. In some embodiments, the filling structure is a double-walled filling structure and the filling agent is injected into the internal space between the outer wall and the inner wall, such that the outer wall conforms to the shape of the aneurysm. The double-walled filling structures are pre-shaped and otherwise adapted to substantially fill the enlarged volume of an aneurysm when filled, particularly a fusiform aneurysm, leaving a lumen in place for blood flow. In some embodiments, the outer wall of the double-walled filling structure is degradable and degrades within the body over a period of time, leaving behind, for example, a hardened or cured polymer filling. In some embodiments, the filling agent (e.g., fluid, polymer, or a combination thereof) is injected directly into the patent aneurysmal space and surrounds the endovascular graft system. Injecting the filling agent directly into the patent aneurysmal space provides the ability to apply pressure directly to the thrombus or wall of the segment of the blood vessel being treated, further aiding in the displacement of pro-inflammatory molecules from the treatment site.

C. Acute Thrombus Pressurization

During EVAS deployment, in various embodiments, endobags are pressurized to a supra-systolic target in order to achieve seal and fixation of the graft system. Van Noort et al., Vasc. 25(5):542-548 (2017) have shown that intraluminal abdominal aortic aneurysm thrombus may undergo a displacement of fluid when exposed to physiological pressures in the short term. The application of pressure on mature thrombus during aneurysm sealing may facilitate the displacement of biologically active fluid within the thrombus into distal circulation, thereby reducing the amount and activity of pro-inflammatory agents remaining in the thrombus. Less active thrombus within the aneurysm may result in reduced PIS. Accordingly, in one aspect, the present technology is directed to methods and systems for the endoluminal treatment of aneurysms, particularly aortic aneurysms including both abdominal aortic aneurysms (AAA's) and thoracic aortic aneurysms (TAA's), including exerting an effective amount of pressure on the intraluminal thrombus or the vessel wall of the segment of the blood vessel to be treated to displace biological fluid from the thrombus or the vessel wall, thereby reducing the inflammatory response associated with the treatment.

Figure 7:
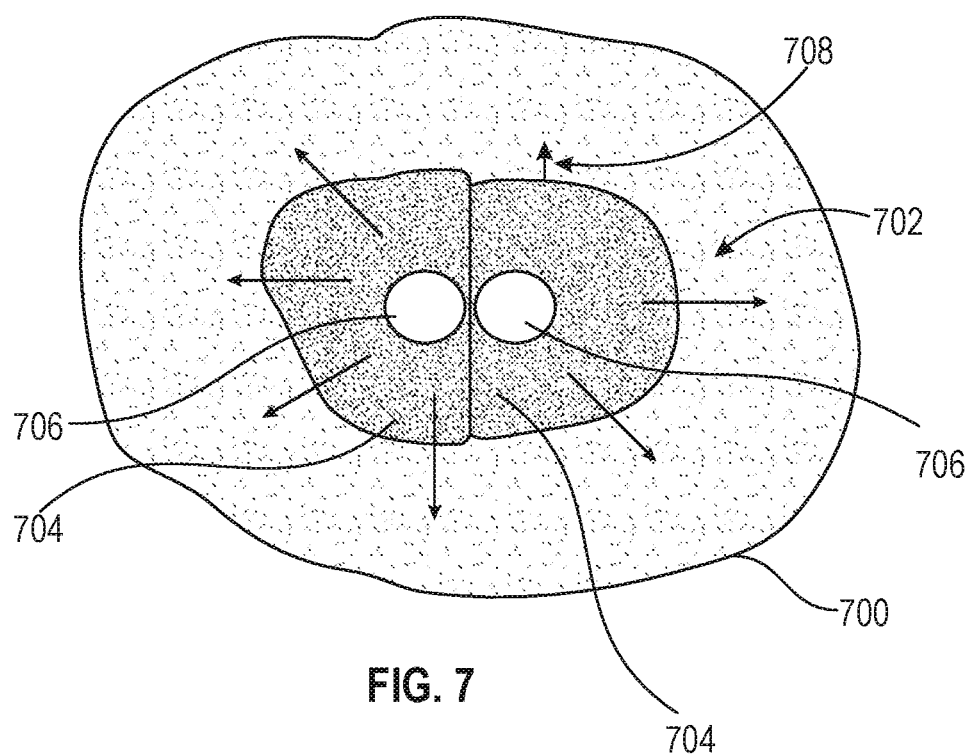
FIG. 7 depicts acute pressurization of thrombus to displace biologically active fluid from the thrombus and/or wall.

In some embodiments, the present technology is directed to systems and methods of treating an aneurysm that comprise filling the patent aneurysmal space with a filling agent (e.g., a gas, a fluid, a polymer, or a combination thereof) such that the acute pressure applied to the thrombus and/or wall of the blood vessel displaces biologically active fluid from the thrombus and/or wall (FIG. 7). This displacement of fluid from the thrombus and/or wall may reduce the overall level and activity of pro-inflammatory molecules (e.g., pro-inflammatory cytokines such as but not limited to tumor necrosis factor alpha (TNF-α) or cyclophilin A, and angiotensin II; and reactive oxygen and nitrogen species (ROS/RNS)). In some embodiments, the filling agent is a curable polymer, which after curing, will have a fixed shape. The polymers may be delivered as liquids, gels, foams, slurries, or the like. In some embodiments, the polymers may be epoxies or other curable two-part systems. In some embodiments, the polymer may comprise a single material which when exposed to the vascular environment changes state over time, typically from zero to ten minutes. In some embodiments, the filling agent is saline. In some embodiments, the filling agent is present within one or more filling structures that form a part of the endovascular graft system.

In some embodiments, the filling structure is a double-walled filling structure and the filling agent is injected into the internal space between the outer wall and the inner wall, such that the outer wall conforms to the shape of the aneurysm. The double-walled filling structures are pre-shaped and otherwise adapted to substantially fill the enlarged volume of an aneurysm when filled, particularly a fusiform aneurysm, leaving a lumen in place for blood flow. In some embodiments, the outer wall of the double-walled filling structure is degradable and degrades within the body over a period of time, leaving behind, e.g., a hardened or cured polymer filling. In some embodiments, the filling agent (e.g., fluid, polymer, or a combination thereof) is injected directly into the patent aneurysmal space and surrounds the endovascular graft system. Injecting the filling agent directly into the patent aneurysmal space provides the ability to apply pressure directly to the thrombus or wall of the segment of the blood vessel being treated, further aiding in the displacement of pro-inflammatory molecules from the treatment site. In some embodiments, the filling agent is a gas and the process of filling is a dynamic process that ensures that pressure is maintained on the thrombus and/or wall for a finite period of time. In some embodiments, the outer wall of the double-walled filling structure comprises features that allow the outer wall to better adhere to the thrombus and/or wall to more effectively apply and maintain an outward force on the thrombus and/or wall. In some embodiments, the outer wall may be partially or entirely modified to promote tissue ingrowth or mechanical interlocking with the inner surface of the aneurysm. Such surface modifications may include surface roughening, surface stippling, surface flocking, fibers disposed over the surface, foam layers disposed over the surface, rings, and the like. It is also possible to provide biologically active substances over all or a portion of the external surface of the graft system, such as thrombogenic substances, tissue growth promotants, biological adhesives, and the like. It would further be possible to provide synthetic adhesives, such as pharmaceutically acceptable polyacrylamides, over the surface of the system to enhance adherence.

In some embodiments, the volume of the filling agent decreases over time, but with sufficient adhesion, such that the reduction in the volume of the filling promotes sac regression.

In some embodiments, a staged or algorithmically based pressure profile is obtained during filling to optimize pressure application to the thrombus and/or wall of the blood vessel. This may be accomplished with a priori knowledge of aneurysm features, such as wall thicknesses throughout the length of the aneurysm, which would inform the algorithm. This information may be obtained prior to implant by a computed tomography (CT) scan or magnetic resonance imaging (MRI) evaluation of the thrombus and/or wall or post or during implantation by sensors. The sensors may be electrical, magnetic, mechanical, or optical sensors that sense information and relay it through a feedback loop to the algorithm.

In some embodiments, the aneurysmal space will be filled with the filling agent at a pressure ranging from about 80 mm Hg to about 1000 mm Hg. In some embodiments, the pressure ranges from about 80-200, about 120-300, about 200-400, about 400-600, about 600-800, or about 800-1000 mm Hg. In some embodiments, the pressure exceeds the systolic pressure. The upper limit of the pressure applied will be determined by the ability of the aneurysm wall to sustain the pressure without rupturing.

In some embodiments, the endovascular graft system is designed to promote the formation of a contiguous polymer mass. In some embodiments, this may be achieved by reducing or eliminating additional structures between the filling agent and the aneurysmal space so that the filling agent is able to more efficiently exert and transmit an outward pressure to the thrombus and/or wall of the blood vessel. In some embodiments, the filling agent is a polymer that exhibits improved aggregation into a single contiguous mass that is able to efficiently exert and transmit an outward pressure to the thrombus and/or wall of the blood vessel.

In some embodiments, the methods and systems of the present technology comprise administering or delivering an agent that promotes rapid maturation of thrombus at the segment of the blood vessel being treated. Any suitable thrombogenic agent known in the art may be employed. Without being bound by theory, conversion of loose thrombus into a contiguous solid thrombus allows it to be pressurized more easily. Moreover, therapeutic agents may be delivered directly into the aneurysm space or introduced with the prosthesis. Accordingly, in an exemplary embodiment, the outer surface of the outer wall of the filling structure comprises a therapeutic agent. In another exemplary embodiment, a therapeutic agent is directly introduced into the aneurysmal space before filling the fillable structure.

D. Chronic Thrombus Pressurization

After EVAS deployment, in various embodiments, even though the hydrostatic pressure within the endobag will approach zero as the polymer cures, the pressure applied to the surrounding structures will be maintained chronically. The presence of this sustained residual net outward pressure on either existing mature thrombus or the aneurysm wall by the polymer filled endobag may reduce or abolish the ability of thrombus to facilitate inflammatory pathways, possibly by reducing extracellular fluid collection or diminishing any factors promoting angiogenesis within the thrombus. Bioactivity of the thrombus may then be lessened in the absence of a requisite medium. Accordingly, in one aspect, the present technology is directed to methods and systems for the endoluminal treatment of aneurysms, particularly aortic aneurysms including both abdominal aortic aneurysms (AAA's) and thoracic aortic aneurysms (TAA's), including exerting an effective amount of pressure on the intraluminal thrombus or the vessel wall of the segment of the blood vessel to be treated to displace biological fluid from the thrombus or the vessel wall, thereby reducing the inflammatory response associated with the treatment.

Figure 8:
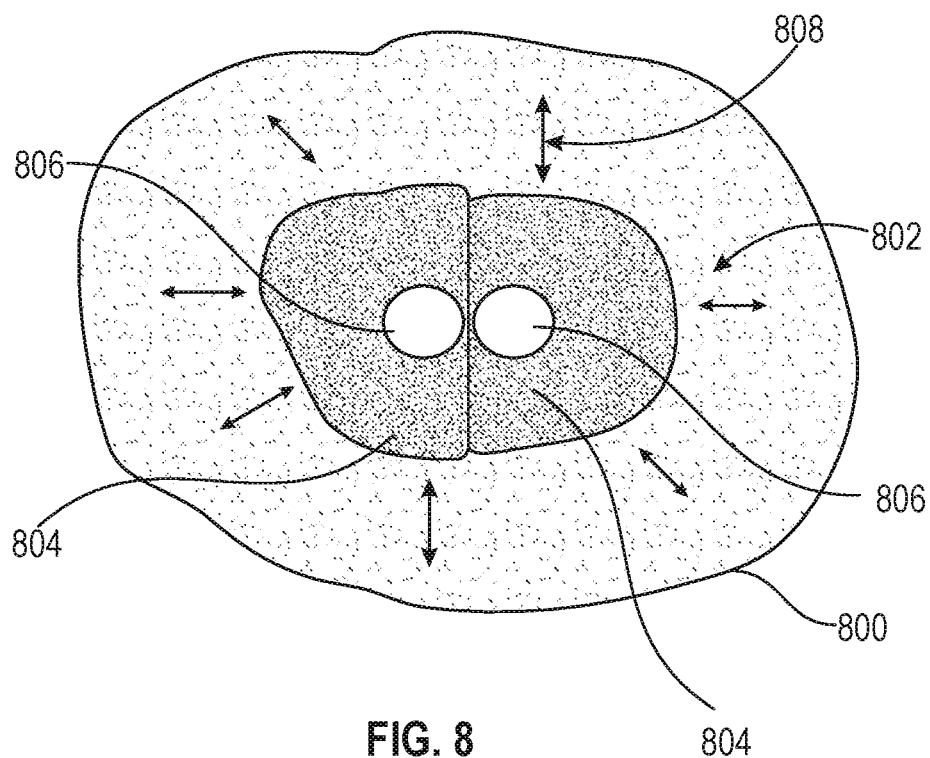
FIG. 8 depicts chronic pressurization of thrombus after deployment of an endovascular graft system to displace biologically active fluid from the thrombus and/or wall and to reduce extracellular fluid collection.

In some embodiments, the present technology is directed to systems and methods of treating an aneurysm that comprise filling the patent aneurysmal space with a filling agent (e.g., a gas, a fluid, a polymer, or a combination thereof) such that the chronic pressure applied to the thrombus and/or wall of the blood vessel displaces biologically active fluid from the thrombus and/or wall (FIG. 8). This displacement of fluid from the thrombus and/or wall in a chronic manner may reduce the overall level and activity of pro-inflammatory molecules (e.g., pro-inflammatory cytokines such as but not limited to tumor necrosis factor alpha (TNF-α) or cyclophilin A, and angiotensin II; and reactive oxygen and nitrogen species (ROS/RNS)). In some embodiments, the filling agent is a curable polymer, which after curing, will have a fixed shape. The polymers may be delivered as liquids, gels, foams, slurries, or the like. In some embodiments, the polymers may be epoxies or other curable two-part systems. In some embodiments, the polymer may comprise a single material which when exposed to the vascular environment changes state over time, typically from zero to ten minutes. In some embodiments, the filling agent is saline. In some embodiments, the filling agent is present within one or more filling structures that form a part of the endovascular graft system.

In some embodiments, the filling structure is a double-walled filling structure and the filling agent is injected into the internal space between the outer wall and the inner wall, such that the outer wall conforms to the shape of the aneurysm. The double-walled filling structures are pre-shaped and otherwise adapted to substantially fill the enlarged volume of an aneurysm when filled, particularly a fusiform aneurysm, leaving a lumen in place for blood flow. In some embodiments, the outer wall of the double-walled filling structure is degradable and degrades within the body over a period of time, leaving behind, e.g., a hardened or cured polymer filling that maintains a chronic pressure against the thrombus and/or vessel wall. In some embodiments, the filling agent (e.g., fluid, polymer, or a combination thereof) is injected directly into the patent aneurysmal space and surrounds the endovascular graft system. Injecting the filling agent directly into the patent aneurysmal space provides the ability to apply pressure directly to the thrombus or wall of the segment of the blood vessel being treated, further aiding in the displacement of pro-inflammatory molecules from the treatment site. In some embodiments, the filling agent is a gas and the process of filling is a dynamic process that ensures that pressure is maintained on the thrombus and/or wall for a finite period of time. In some embodiments, the outer wall of the double-walled filling structure comprises features that allow the outer wall to better adhere to the thrombus and/or wall to more effectively apply and maintain an outward force on the thrombus and/or wall chronically. In some embodiments, the outer wall may be partially or entirely modified to promote tissue ingrowth or mechanical interlocking with the inner surface of the aneurysm. Such surface modifications may include surface roughening, surface stippling, surface flocking, fibers disposed over the surface, foam layers disposed over the surface, rings, and the like. It is also possible to provide biologically active substances over all or a portion of the external surface of the graft system, such as thrombogenic substances, tissue growth promotants, biological adhesives, and the like. It would further be possible to provide synthetic adhesives, such as pharmaceutically acceptable polyacrylamides, over the surface of the system to enhance adherence.

In some embodiments, the chronic pressure exerted by the endovascular graft on the thrombus and/or vessel wall ranges from about 80-200, about 80-100, about 100-120, about 120-140, about 140-160, about 160-180, or about 180-200 mm Hg.

In some embodiments, the volume of the filling agent decreases over time, but with sufficient adhesion, such that the reduction in the volume of the filling promotes sac regression.

In some embodiments, a staged or algorithmically based pressure profile is obtained during filling to optimize pressure application to the thrombus and/or wall of the blood vessel. This may be accomplished with a priori knowledge of aneurysm features, such as wall thicknesses throughout the length of the aneurysm, which would inform the algorithm. This information may be obtained prior to implant by CT or MRI evaluation of the thrombus and/or wall or post or during implantation by sensors. The sensors may be electrical, magnetic, mechanical, or optical sensors that sense information and relay it through a feedback loop to the algorithm. This will also inform the pressure that will be chronically exerted by the graft system on the thrombus and/or vessel wall of the segment of the blood vessel being treated.

In some embodiments, the endovascular graft system is designed to promote the formation of a contiguous polymer mass. In some embodiments, this may be achieved by reducing or eliminating additional structures between the filling agent and the aneurysmal space so that the filling agent is able to more efficiently exert and transmit an outward pressure to the thrombus and/or wall of the blood vessel. In some embodiments, the filling agent is a polymer that exhibits improved aggregation into a single contiguous mass that is able to efficiently exert and transmit an outward pressure to the thrombus and/or wall of the blood vessel in a chronic manner.

In some embodiments, the methods and systems of the present technology comprise administering or delivering an agent that promotes rapid maturation of thrombus at the segment of the blood vessel being treated. Without being bound by theory, conversion of loose thrombus into a contiguous solid thrombus allows it to be pressurized more easily.

In some embodiments, the systems of the present technology comprise additional support structures or surface modifications in the flow lumen of the endovascular graft system to guard against lumen collapse and thus ensure application of pressure to the thrombus and/or wall chronically. In some embodiments, the systems comprise braid reinforcement layers, filament reinforcement layers, and the like. In some embodiments, the systems comprise surface modifications such as rings and the like.

E. Interaction of Materials

Figure 9:
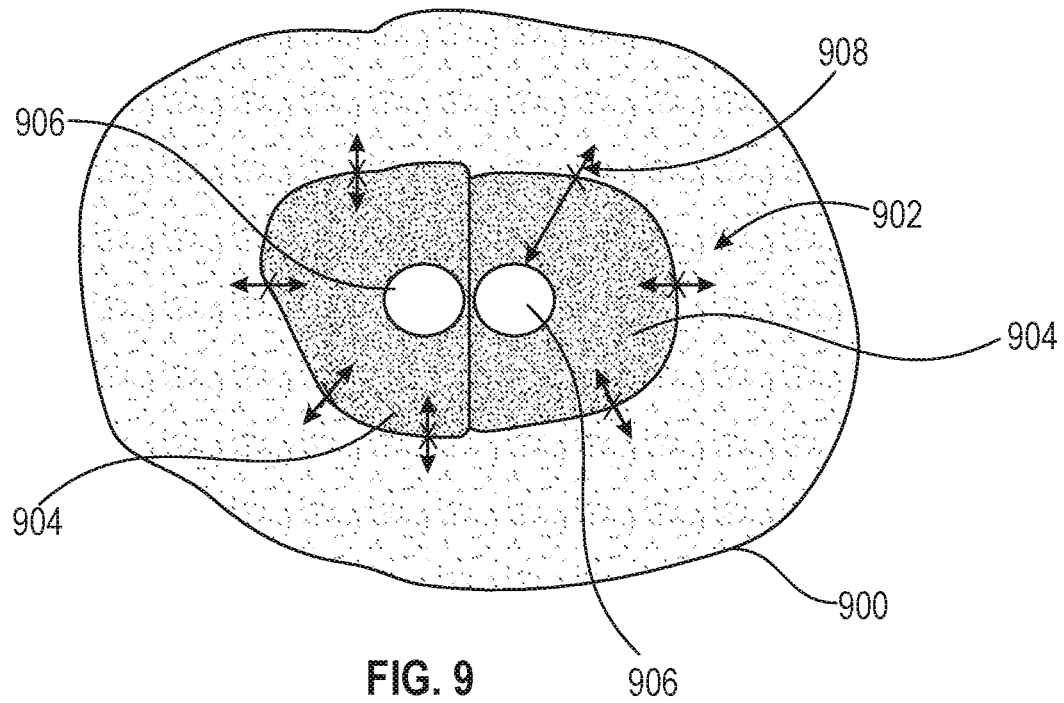
FIG. 9 depicts the reduction or elimination of communication between a flow lumen and thrombus by optimizing the materials used in an endovascular graft system.

Historically, stent graft materials have been limited to polyesters and ePTFE due to their known biocompatibility. Though inert in terms of a severe immune response, the presence of any foreign body will result in some biochemical reaction. Without being bound by theory, substituting the chemical functional groups and micro porosity of polyester and ePTFE materials with an impervious polyurethane material in various embodiments may mitigate a large volume pro-inflammatory host tissue response or scar tissue formation by eliminating all communication between the flow lumen and the thrombus (FIG. 9). This would reduce the overall sustained inflammatory response throughout the vascular system. Accordingly, in one aspect, the present technology provides endovascular graft systems including stent grafts comprising polyurethane to provide a lumen for blood flow. In some embodiments, the endovascular graft systems include stent grafts comprising polyethylene glycol or collagen to provide a lumen for blood flow.

Examples of polyurethanes include Thoralon® (THORATEC, Pleasanton, Calif.), BIOSPAN®, BIONATE®, ELASTHANE®, PURSIL®, and CARBOSIL® (POLYMER TECHNOLOGY GROUP, Berkeley, Calif.). As described in U.S. Pat. No. 6,939,377, the entire contents of which are incorporated herein by reference, Thoralon® is a polyetherurethane urea blended with a siloxane-containing surface modifying additive. Specifically, the polymer is a mixture of base polymer BPS-215 and an additive SMA- 300. The concentration of additive may be in the range of 0.5% to 5% by weight of the base polymer. The BPS-215 component (THORATEC) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). Thoralon® has been used in certain vascular applications and is characterized by thromboresistance, high tensile strength, low water absorption, low critical surface tension, and good flex life. Thoralon® is believed to be biostable and to be useful in vivo in long term blood contacting applications requiring biostability and leak resistance. Because of its flexibility, Thoralon® is useful in larger vessels, such as the abdominal aorta, where elasticity and compliance is beneficial. Other polyurethane ureas may be used in addition to Thoralon®. In addition to polyurethane ureas, other polyurethanes, e.g., those having a chain extended with diols, may be used as the graft material. Polyurethanes modified with cationic, anionic, and aliphatic side chains may also be used. See, for example, U.S. Pat. No. 5,017,664, the entire contents of which are incorporated herein by reference. The polyurethanes may also be end-capped with surface active end groups, such as, for example, polydimethylsiloxane, fluoropolymers, polyolefin, polyethylene oxide, or other suitable groups. See, for example, the surface active end groups disclosed in U.S. Pat. No. 5,589,563, the entire contents of which are incorporated herein by reference. In some embodiments, the graft material may contain polyurethane having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIO-MATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. Examples of siloxane-polyurethanes are disclosed in U.S. Pat. Pub. No. 2002/0187288 A1, the entire contents of which are incorporated herein by reference.

F. Surface Area

There is evidence of deposits on the ePTFE lining the interior of the stents. Therefore, reducing the internal surface area available for deposits in accordance with various embodiments may mitigate the inflammatory response by reducing the presence of pro-inflammatory deposits on the interior of the stents. In some embodiments, the endovascular graft system of the present disclosure comprises one or more stents forming a lumen(s) in place for blood flow with a total diameter less than 20 mm. In some embodiments, the total diameter is about 5, 6, 7, 8, 9, 10, 11, 12, 13, 14, 15, 16, 17, 18, or 19 mm.

In any of the embodiments described herein, the endovascular graft system may be fixed at the proximal and/or distal sealing locations (e.g., at the neck and iliacs when treating an infrarenal aortic aneurysm). Additional sealing or anchoring mechanisms include but are not limited to stents, scaffolds, hooks, barbs, seals, sealing cuffs, and the like. For sealing cuffs or stents which extend proximately of infrarenal prosthesis, it may be desirable to provide openings or ports to allow the anchoring or sealing devices to extend over the renal ostia while penetrating blood flow into the renal arteries. The sealing or anchoring devices will typically be attached to and/or overlap with the filling structure of the prosthesis and will provide for a smooth transition from the aortic and/or iliac lumens into the tubular lumens provided by the deployed filling structures.

In any of the embodiments described herein, the endovascular graft system may be modified in other ways to enhance placement within the aneurysmal space. In some embodiments, the external surfaces of the systems may be partially or entirely modified to promote tissue ingrowth or mechanical interlocking with the inner surface of the aneurysm. Such surface modifications may include surface roughening, surface stippling, surface flocking, fibers disposed over the surface, foam layers disposed over the surface, rings, and the like. It is also possible to provide biologically active substances over all or a portion of the external surface of the graft system, such as thrombogenic substances, tissue growth promotants, biological adhesives, and the like. It would further be possible to provide synthetic adhesives, such as pharmaceutically acceptable polyacrylamides, over the surface of the system to enhance adherence.

In any of the embodiments described herein, the volume of the filling agent may decrease over time, but with sufficient adhesion, such that the reduction in the volume of the filling promotes sac regression.

In any of the embodiments described herein, the methods and systems of the present technology may be further modified to allow biological fluid to escape distally out of the aneurysmal space. In some embodiments, the endovascular graft system comprises a channel for the fluid to escape. In an exemplary embodiment, the filling structure comprises channels for fluid flow proximally or distally.

In any of the embodiments described herein, the methods and systems of the present technology may further include a step of mechanically aspirating thrombus from the aneurysmal space. This may be performed using the endovascular graft system or may be accomplished separately. Reducing the thrombus in this manner will reduce inflammation associated with the deployment of the endovascular graft system.

Any of the embodiments described herein can be combined with therapies such as anti-platelet therapy, statin therapy, or ACE inhibitor therapy. Such therapies are known in the art and it is within the purview of the skilled artisan to select a suitable therapy.

Graft Systems

In one aspect, the present technology provides methods and systems for the endoluminal treatment of aneurysms, particularly aortic aneurysms including both abdominal aortic aneurysms (AAA's) and thoracic aortic aneurysms (TAA's). In particular, treatment of thoracic, abdominal, infrarenal, juxtarenal, pararenal or paravisceral aneurysms is contemplated herein. The systems include prostheses which comprise double-walled filling structures which are pre-shaped and otherwise adapted to substantially fill the enlarged volume of an aneurysm when filled, particularly a fusiform aneurysm, leaving a lumen in place for blood flow. In some embodiments, the systems comprise single-walled structures with a lumen for blood flow.

An exemplary single prosthesis system comprising a filling structure mounted over a delivery catheter is illustrated in FIG. 1. A system 10 constructed for delivering a double-walled filling structure 12 to an aneurysm includes the filling structure and a delivery catheter 14 having an expandable element 16, typically an inflatable balloon, at its distal end. The catheter 14 will comprise a guidewire lumen 18, a balloon inflation lumen (not illustrated) or other structure for expanding other expandable components, and a filling tube 20 for delivering a filling agent to an internal space 22 of the double-walled filling structure 12. The internal space 22 is defined between an outer wall 24 and inner wall 26 of the filling structure. Upon inflation with the filling agent, the outer wall 24 will expand radially outwardly, as shown in broken line, as will the inner wall 26, also shown in broken line. Expansion of the inner wall 26 defines an internal lumen 28. The expandable balloon or other structure 16 will be expandable to support an inner surface of the lumen 28, as also in broken line in FIG. 1. The filling agent may be a gas, a fluid, a polymer, or a combination thereof.

Figure 2:
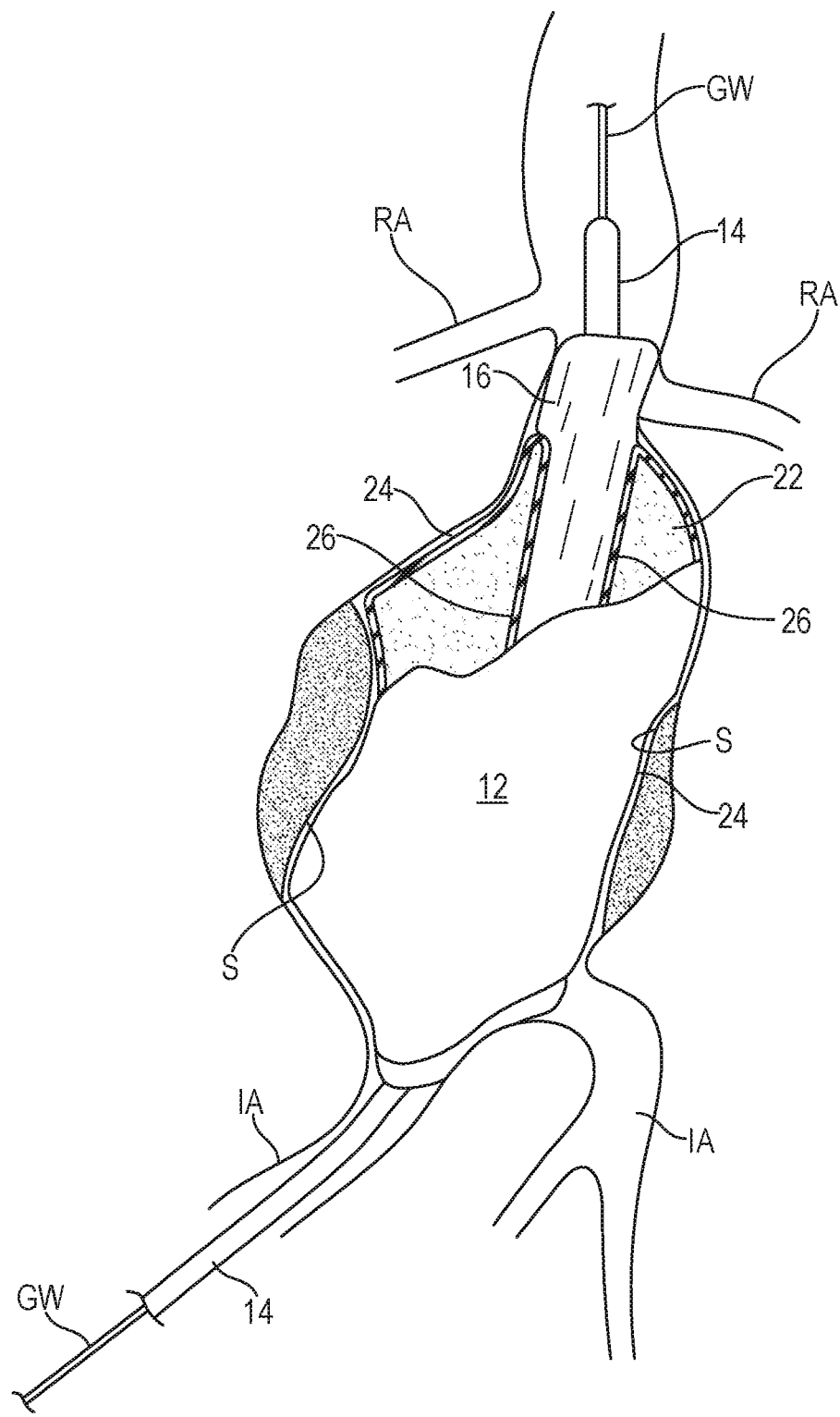
FIG. 2 illustrates use of an embodiment of the prosthesis system of FIG. 1 for treating an infrarenal abdominal aortic aneurysm.

The treatment system 10 of FIG. 1 may be utilized to treat the complex geometry of the transmural abdominal aortic aneurysm (AAA) by first positioning the delivery catheter 14 to place the double-walled filling structure 12 (in its unfilled configuration) generally across the aneurysm from the region of the aorta beneath the renal arteries (RA) to a region over the iliac arteries (IA), as is seen in FIG. 2. The delivery catheter 14 may be introduced over a guidewire (GW) through a puncture in the patient's groin accessing the iliac artery by the Seldinger technique. After the double-walled filling structure 12 is properly positioned, a filling agent is introduced into the internal space 22 filling of the inner space 22 expands the outer wall 24 of the structure outwardly so that it conforms to the inner surface (S) of the aneurismal space. Before, during, or after filling of the double-walled filling structure 12 with inflation medium, the balloon 16 or other expansible structure will also be inflated or expanded to open the tubular lumen defined by the interior of the inner wall 26. The filling agent may be a gas, a fluid, a polymer, or a combination thereof. In some embodiments, the filling agent is saline. In some embodiments, the filling agent is a gas.

Figure 3:
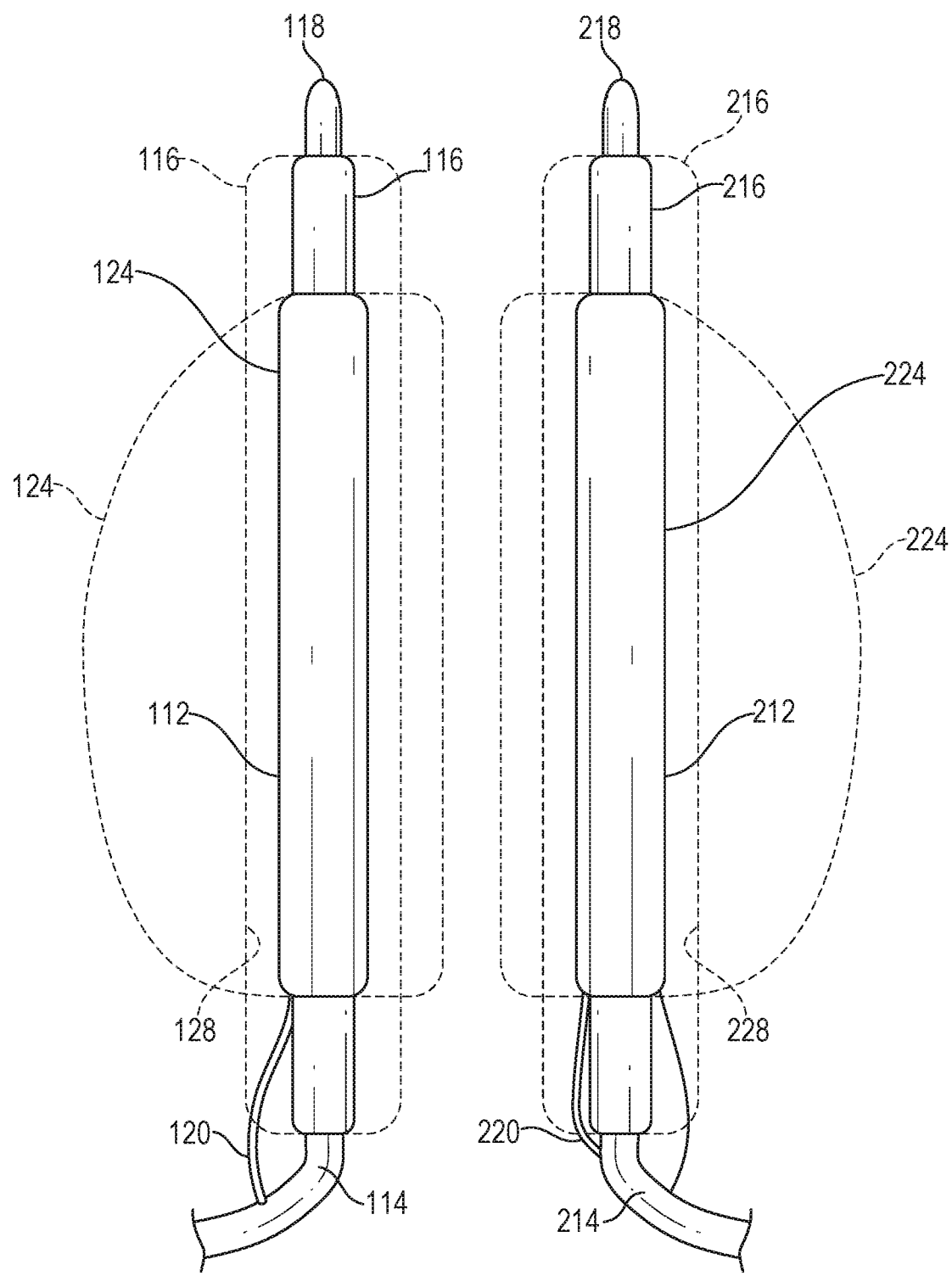
FIG. 3 illustrates a system including a pair of prostheses for delivery to an infrarenal abdominal aortic aneurysm, where each prosthesis comprises a filling structure mounted on a delivery catheter.

In any embodiments, a pair of double-walled filling structures can be used to treat aortic aneurysms (e.g. infra-renal aortic aneurysms), instead of only a single filling structure as illustrated in FIG. 2. A system comprising such a pair of filling structures is illustrated in FIG. 3 which includes a first filling structure 112 and a second filling structure 212. Each of the filling structures 112 and 212 are mounted on delivery catheters 114 and 214, respectively. The components of the filling structures 112 and 212 and delivery catheters 114 and 214 are generally the same as those described previously with respect to the single filling structure system 10 of FIG. 1. As shown in FIG. 3, the delivery catheters 114 and 214 comprise guidewire lumens 118 and 218, respectively. The expanded inner walls 128 and 228 are supported with the balloons 116 and 216, respectively. The filling structures may be filled using flow tubes 120 and 220. A principal difference between the filling structures 112 and 212, on the one hand, and the filling structure 12 of FIG. 1 is that the pair of filling structures will generally have asymmetric configurations which are meant to be positioned adjacent to each other within the aneurismal space and to in combination fill that space. After filling the filling structures 112 and 212 of FIG. 3 with a filling agent, the delivery catheters 114 and 214 are removed, respectively. The filling structures will then provide a pair of tubular lumens opening from the aorta beneath the renal arteries to the right and left iliac arteries. The ability of the filling structures 112 and 212 to conform to the inner surface of the aneurysm, helps the structures to remain immobilized within the aneurysm with little or no migration. The filling agent may be a gas, a fluid, a polymer, or a combination thereof. In some embodiments, the filling agent is a curable polymer that hardens within the filling structure. In some embodiments, the filling agent is saline. In some embodiments, the filling agent is a gas.

Figure 4:
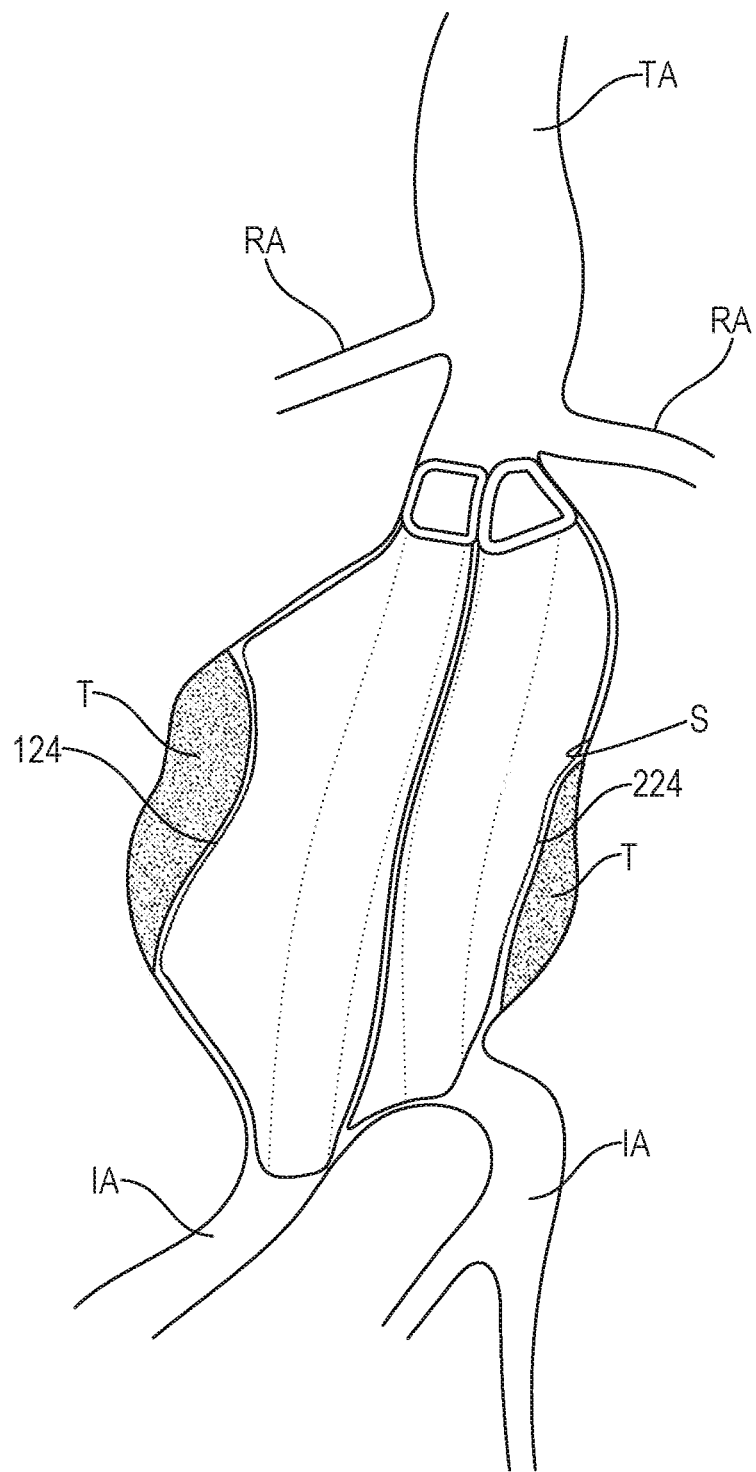
FIG. 4 illustrates the use of the system of FIG. 3 for treating an infrarenal abdominal aortic aneurysm.

FIG. 4 illustrates the stent-graft system of FIG. 3 when deployed. With reference to FIGS. 3 and 4, the outer surfaces 124 and 224 of the filling structures 112 and 212, respectively, contact the aneurysm surface (S) and any thrombus (T) located in the aneurysmal space. In particular, the filling structures 112 and 212 filled with polymeric material can place an effective amount of pressure on the aneurysm surface (S) and/or the thrombus (T) when the stent-graft is expanded.

Further illustrating advantages of the exemplary embodiments, FIGS. 5A and 5B provide a conceptual cross-sectional representation of an aneurysm being treated. In FIG. 5A, the EVAS system provides dual flow lumens 508, each having an expandable structure (endobag) 510 which when expanded places pressure on the existing thrombus 502 located between the expandable structures 510 and an aneurysm wall 500. In contrast, the EVAR system depicted in FIG. 5B allows for new-onset thrombus formation 506 between the existing thrombus 502 on the aneurysm wall 500 and the flow lumen 504.

As described earlier, and in accordance with the exemplary embodiments, the effects of PIS may be mitigated via elimination of perfusion. This concept is illustrated with the aneurysm cross-sectional representation in FIG. 6. As shown, fluid flow (blood) pathways 608 from the circulatory system (not shown) across an aneurysm wall 600 into the thrombus 602 may be eliminated with a filling structure 604. Moreover, the filling structure 604 can act as a barrier to fluid communication between a flow lumen 606 and the thrombus 602.

A conceptual representation for acute thrombus pressurization is provided in FIG. 7. Here, pressure 708 from a filling structure 704 against a thrombus 702 (and aneurysm wall 700) can displace biologically active fluid from the thrombus 702 or aneurysm wall 700. In particular, the radial expansion of the stent-graft (in a lumen 706) can cause the filling structure 704 to place an effective amount of pressure on the thrombus/aneurysm wall. Relatedly, chronic thrombus pressurization is conceptually represented in FIG. 8. Here, pressure 808 is placed on a thrombus 802 (and aneurysm wall 800) with a filling structure 804. Again, radial expansion of the stent-graft in a lumen 806 may result in an effective amount of pressure on the thrombus 802 to displace biological fluid and mitigate the effects of PIS.

Elimination of interaction between a thrombus and flow lumen, as described above, is exemplified in FIG. 9. As shown, the choice of material for the stent-graft forming a lumen 906 can eliminate fluid communication 908 between the lumen 906 and a thrombus 902 within an aneurysm wall 900 (aneurysmal space). This may be accomplished by, among other things, choosing a material with lower porosity, pore size or both. A filling structure 904 can also act as a barrier to fluid flow as well.

In addition to the filling structures described hereinabove, the systems may further include at least a first scaffold separate from the filling structure, where the scaffold can be expanded within the generally tubular lumen which provides the blood flow after the filling structure has been deployed in the aneurysm. The first scaffold will be adapted to expand within at least a first portion of the tubular lumen of the filling structure and may provide one or more specific advantages. For example, the scaffold may support and smooth the inside wall of the tubular lumen which in some cases might otherwise become uneven during hardening of the polymer fill. Scaffolds may also provide for anchoring of the filling structure, particularly at the aortic end of the graft when placed in an AAA. The scaffold may be partly or wholly covered with a membrane in order to form a stent-graft. In such cases, the graft structure may help provide a transition from the blood vessel into the generally tubular lumen of the filling structure from the aortic end. Alternatively, the graft structure could provide one or a pair of transitions out of the iliac end of the filling structure. In a particular example, a graft structure can be used on either side of the filling structure in order to treat additional or continuing aneurysmal regions in the adjacent blood vessel. In any embodiments, the system may include multiple scaffold structures. For example, the system may include at least a first and a second scaffold, one for each of the tubular lumens defined by the first and second double-walled filling structures, respectively. The scaffolds may be adapted to be placed in series, frequently overlapping, or may be adapted to be spaced apart at either or both ends and optionally at regions between the ends.

In various embodiments, a short, stent-like scaffold structure for a single prosthesis system may be used. The scaffold may be implanted in an upper proximal opening of a tubular lumen of a filling structure in order to help anchor the upper end of the structure and prevent intrusion of blood into the region between the outer wall and the inner surface of the aneurysm and to generally improve the transition from the aorta into the tubular lumen. The stent-like structure may include any conventional stent, graft, or other expandable luminal support structure known in the art. For example, the graft may include one or more circumferential inflatable channels extending around the entire circumference of the graft body or may extend partially around the circumference of the graft body. The circumferential inflatable channels may be in communication with each other via a longitudinal inflatable fill channel. The network of inflatable channels may optionally be filled with a hardenable material that may be configured to harden, cure or otherwise increase in viscosity or become more rigid after being injected into the channels. Hardenable inflation materials such as gels, liquids or other flowable materials that are curable to a more solid or substantially hardened state may be used to provide mechanical support to the graft body by virtue of the mechanical properties of the hardened material disposed within the channels. In some embodiments, the filling agent is saline. In some embodiments, the filling agent is a gas.

Figure 10:
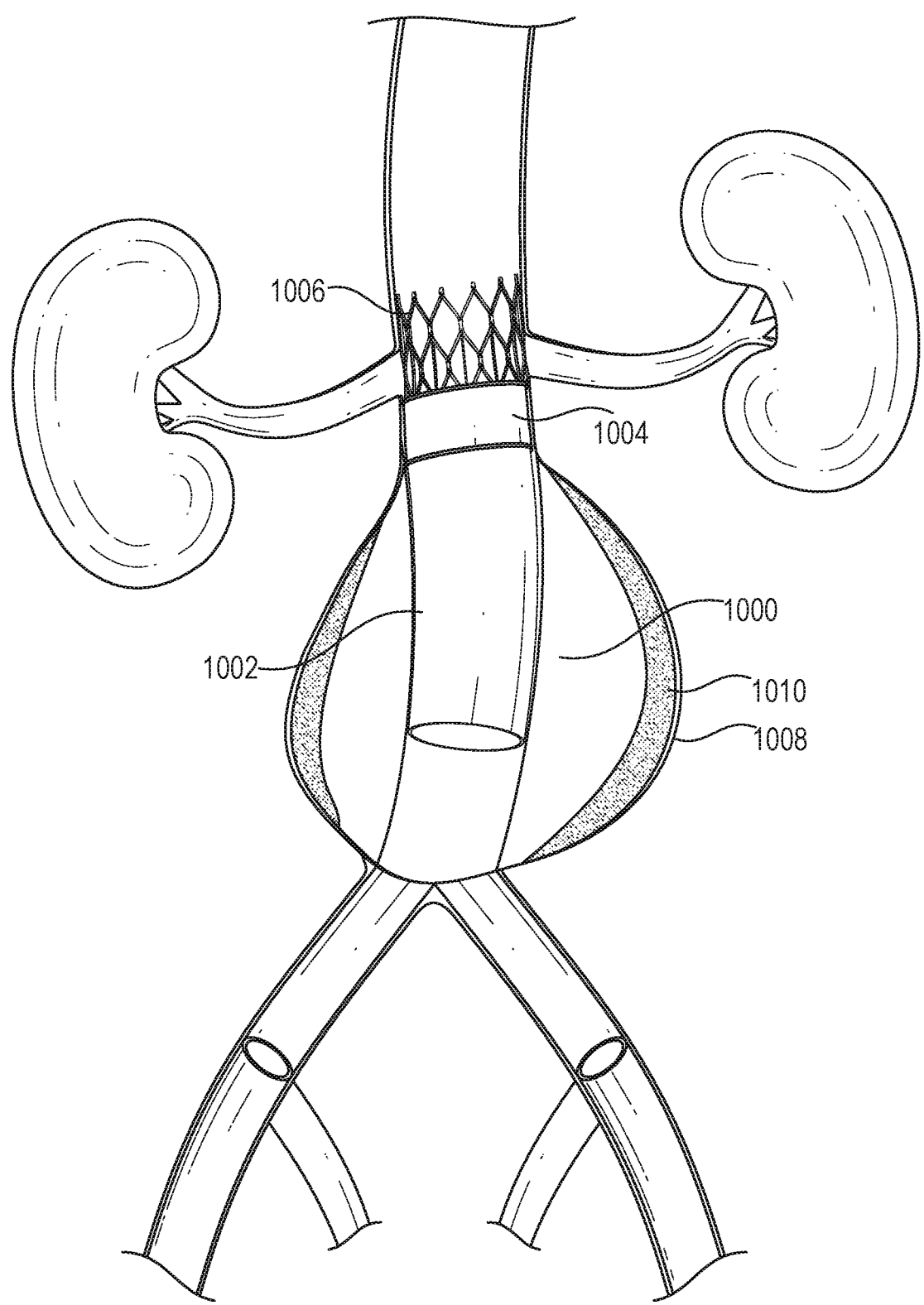
FIG. 10 depicts a stent graft system deployed across an aneurysm in accordance with an exemplary embodiment.

FIG. 10 shows a stent graft system deployed across an aneurysm in accordance with an exemplary embodiment. As shown, a stent-graft prosthesis 1002 is positioned across an aneurysm where a filling structure 1000 is filled with a filling agent and expanded to contact an aneurysm wall 1008 and/or a thrombus 1010 located thereon. The prosthesis 1002 here includes a cuff portion 1004 and an anchoring stent portion 1006 to fix the position of the prosthesis and seal a proximal opening into the aneurysm. In various embodiments, the stent graft system of FIG. 10 is configured to carry out one or more of the (A) space filling; (B) elimination of perfusion; (C) acute thrombus pressurization; (D) chronic thrombus pressurization; (E) interaction of materials; and (F) surface area mechanisms discussed above.

Figure 11:
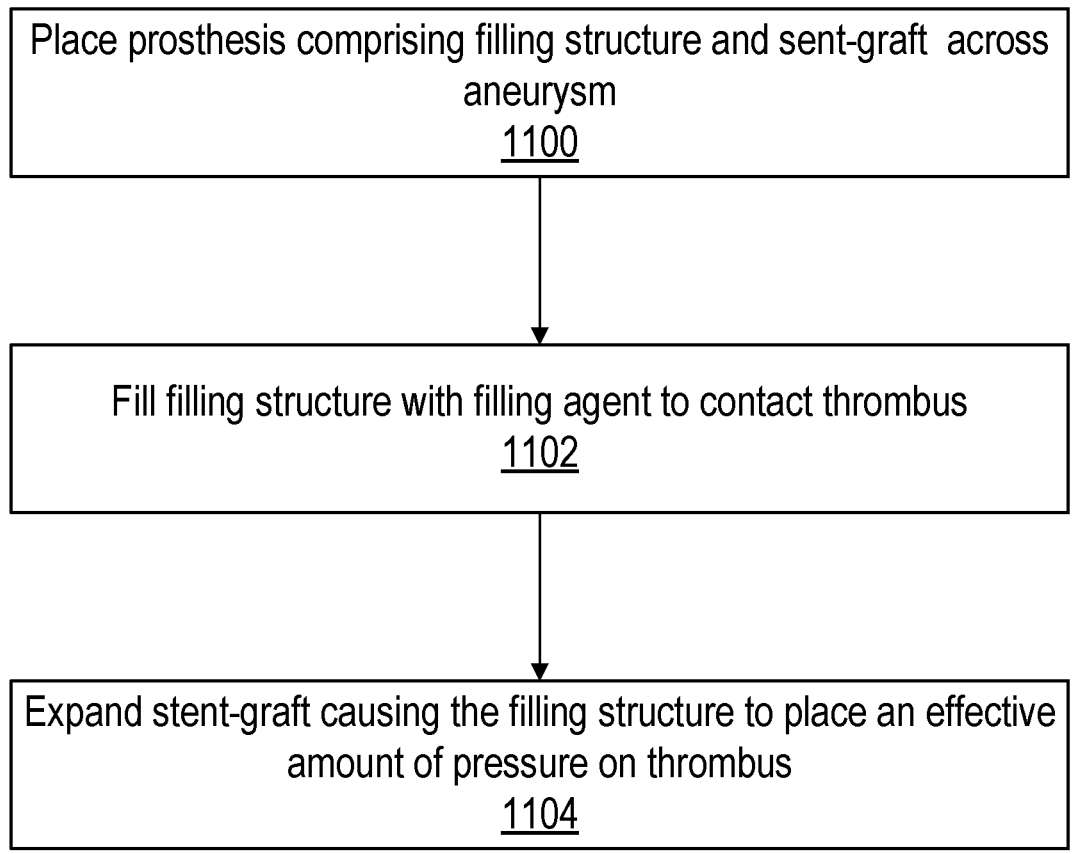
FIG. 11 is a flow diagram illustrating generally the steps of treating an aneurysm and mitigating the effects of post implant syndrome, in accordance with the exemplary embodiments.
Figure 12:
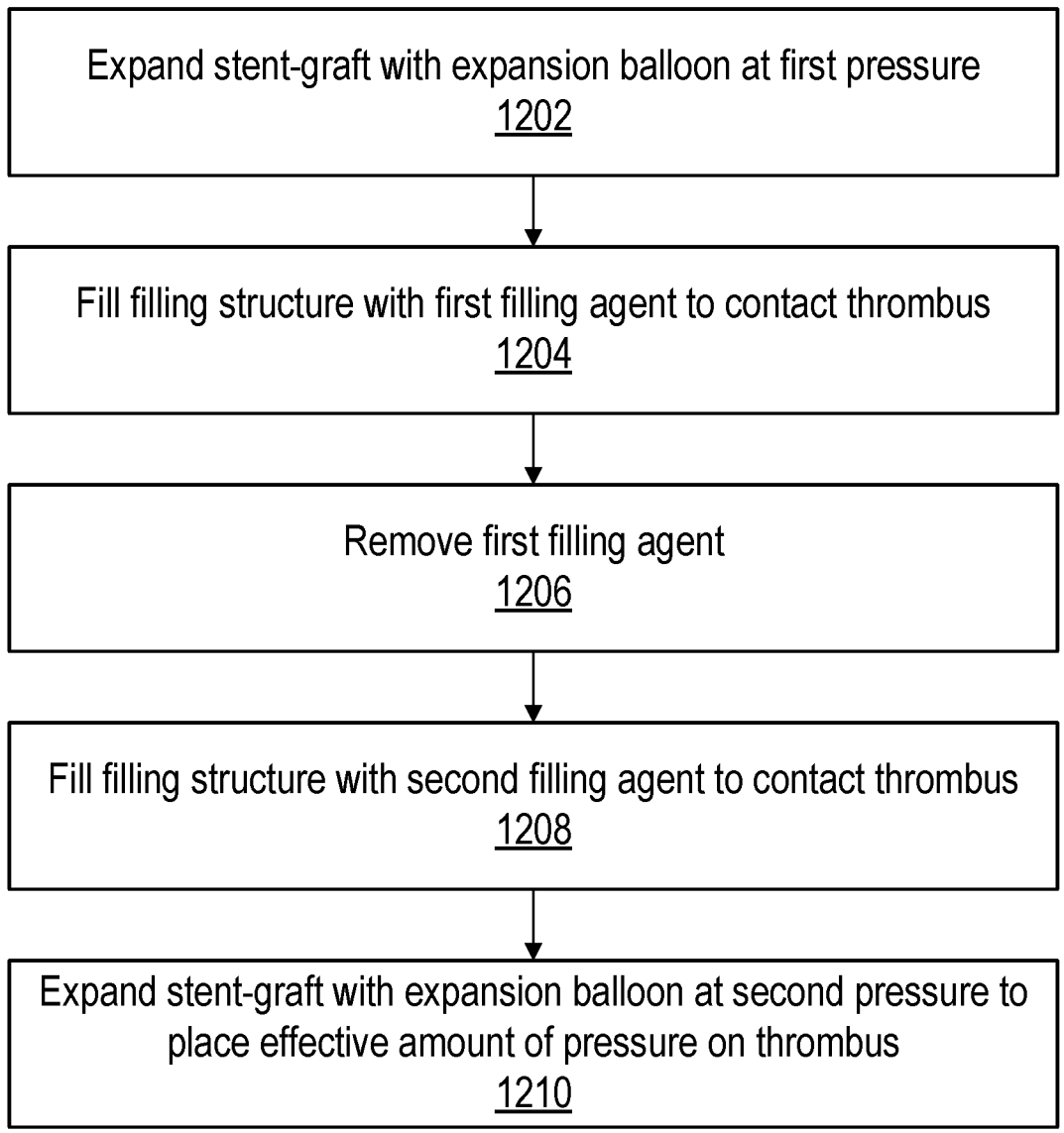
FIG. 12 is a flow diagram illustrating the steps of treating an aneurysm and mitigating the effects of post implant syndrome, in accordance with an exemplary embodiment.
Figure 13:
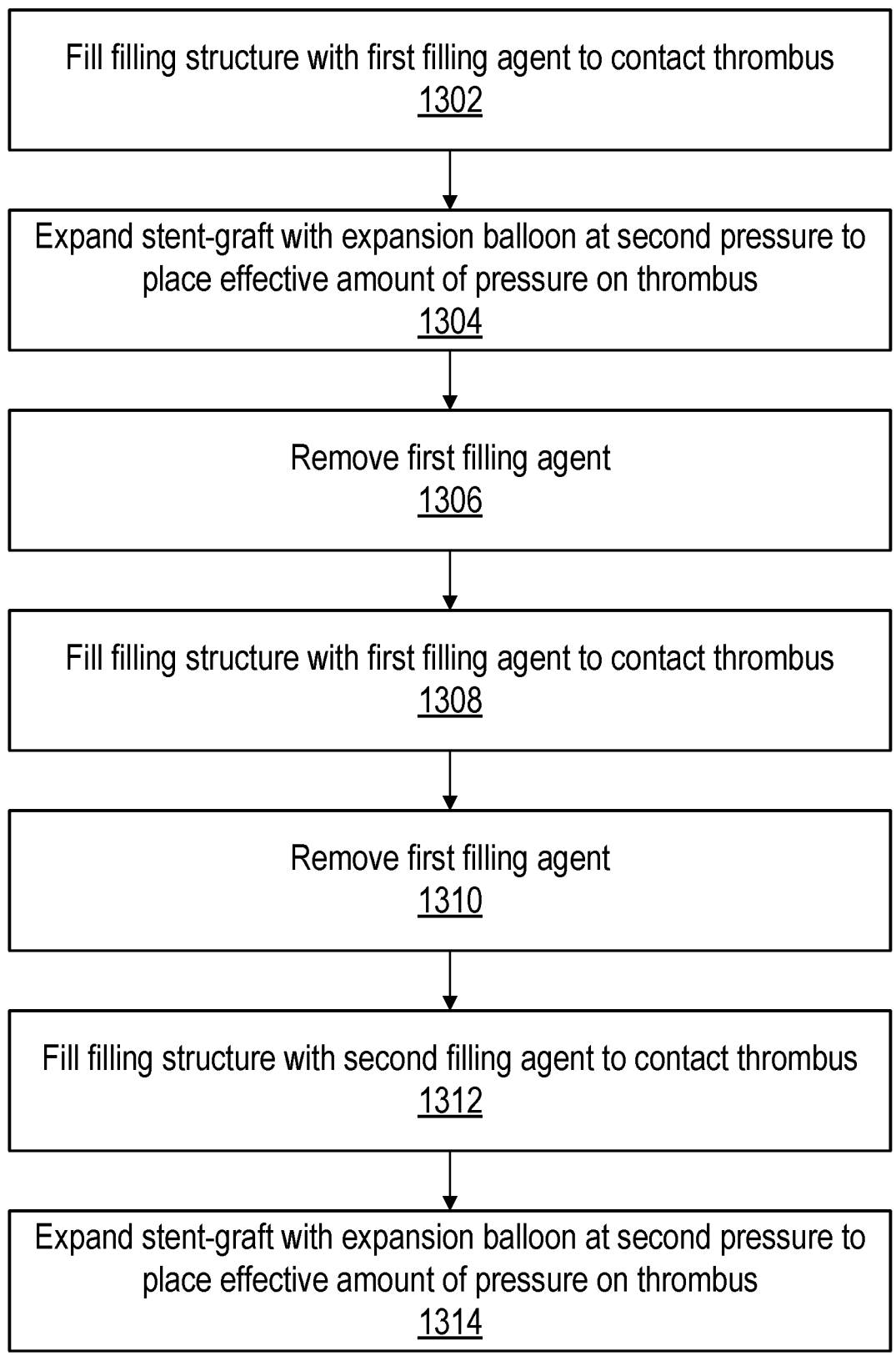
FIG. 13 is a flow diagram illustrating the steps of treating an aneurysm and mitigating the effects of post implant syndrome, in accordance with another exemplary embodiment.

Various embodiments are also exemplified in the flow diagrams of FIGS. 11, 12, and 13. In FIG. 11, a simplified flow diagram is provided where, starting with the step 1100, a prosthesis comprising a filling structure and a stent-graft, is placed across a patient's aneurysm. In the next step 1102, the filling structure is filled with a filling agent to contact a thrombus located in the aneurysm. The filling agent may be a first filling agent or a second filling agent depending on the methodology. The stent-graft of the prosthesis is expanded in the next step 1104 against the filled filling structure. Consequently, the filling structure places an effective amount of pressure on the thrombus.

The order of filling, expanding and/or deploying portions of the prosthesis can vary. For instance, in FIG. 12, the stent-graft is first expanded with an expansion balloon at a first pressure in step 1202. This can provide support for expansion of the filling structure when filled with a first filling agent in step 1204. The first filling agent here may be saline, whereby the amount used to fill the structure can be used as an approximation of the volume of the aneurysmal space. After the first filling agent is removed in step 1206, the filling structure is re-filled with a second filling agent in step 1208. The second filling agent can comprise a curable polymeric material. In the next step, 1210, the stent-graft is again expanded, but this time at a second pressure. The second pressure here is substantially greater than the first pressure. Consequently, as the stent graft is expanded against the filling structure, the outer walls of the filling structure exert an effective amount of pressure against the thrombus.

Another exemplary embodiment is provided in FIG. 13. Beginning with step 1302 a first filling agent is introduced into the filling structure to provide contact with a thrombus in the aneurysmal space. Preferably, the filling agent is saline or another fluid that can be easily introduced and withdrawn. This step can assist in unfurling the filling structure (e.g., endobag) and potentially aid in achieving a better seal, among other things. Moreover, the filling structure may be pre-shaped such that it provides a lumen structure before expansion of the stent-graft. Next, in step 1304, the stent-graft is expanded against the filling structure causing the filling structure outer wall to place an effective amount of pressure on the thrombus. The first filing agent is then removed in step 1306. With the expanded stent-graft now in place, in step 1308 the filling structure is again filled with a first filling agent which may be used to determine the volume of the aneurysm, among other things. This information is used (after removing the filling agent in step 1310) in step 1312 to fill the structure with a second filling agent (e.g. curable polymer) to contact the thrombus in the aneurysmal space. Finally, the stent graft is re-expanded in step 1314 at a second pressure against the filling structure, thereby causing the filling structure to place an effective amount of pressure on the thrombus.

In an exemplary embodiments, the filling structure filled with the first or second filling agent may contact and place an effective amount of pressure on a thrombus (or thrombi) in the aneurysmal space. For instance, when filled with a filling agent solution, the filling pressure may be sufficient to cause the outer walls to place an effective amount of pressure on the thrombus. Expansion of the stent-graft against the filling structure wall can then result in additional effective amount of pressure. Thus, the present disclosure contemplates multiple instances where an effective amount of pressure is applied to a thrombus.

The first filling agent filling agent can comprise any fluid that, when used with the filling structure, allows for sealing the aneurysm, exerting an effective amount of pressure on a thrombus and measurement of the aneurysm volume, among other things. Suitable candidates can include gases, liquids, or a combination thereof. Preferably, the filling agent is biocompatible and not harmful to the patient if a leakage occurs. In an exemplary embodiment, the first filling agent is an aqueous solution, such as saline.

The second filling agent can comprise any fluid that, when used with the filling structure, allows for sealing the aneurysm, providing structural support for the prosthesis, and placing an effective amount of pressure on a thrombus in the aneurysmal space, among other things. Suitable candidates include, but are not limited to polymeric materials. In particular, the second filling agent may be a multi-component system where each component is introduced into the filling structure at different times. Alternatively, the components may be mixed prior to delivery. A non-limiting example of the second filling agent includes Polyethylene glycol (PEG)-based polymers, which may be injected into the filling structure as a two-part solution. The solution can be mixed at the time of delivery to create a compact network of polymeric chains.

As previously discussed, the effective amount of pressure applied to a thrombus, aneurysm wall, or both may be described numerically. That is, the pressure may be a certain pressure value or pressure range. Moreover, and without being bound by any theory, the pressure used to fill the filling structure, fill the expansion balloon, or both may be used as an approximation of the pressure applied to a thrombus or portion of the aneurysm wall. Of course, each patient aneurysm is different, and the pressure may be modified based on the imaging and analysis of the patient anatomy as well. This can include identification of the size, shape and location of the thrombus. With that said, in the exemplary embodiments, the effective amount of pressure applied is at least about 180 mm Hg. In an exemplary embodiment, the effective amount of pressure is between about 180 mm Hg and about 300 mm Hg, including every integer value in the range.

A first pressure and second pressure for expanding the expansion balloon (and the stent-graft) may be described at different steps of carrying out the exemplary methods. For instance, the first pressure may be used for the expansion balloon to expand the stent-graft before or after the filling structure is filled with the first filling agent. In an exemplary embodiment, the first pressure is at least about 180 mm Hg. In another exemplary embodiment, the first pressure is between about 180 mm Hg and about 300 mm Hg including every integer value in the range. The second pressure is substantially greater than the first pressure and is also used to expand the expansion balloon. In particular, the second pressure can be applied when the filling structure is filled with the first filing agent and in some instances, when filled with the first filling agent. In an exemplary embodiment, the second pressure is at least about 190 mm Hg. In another exemplary embodiment, the first pressure is between about 190 mm Hg and about 300 mm Hg including every integer value in the range. Accordingly, and without being bound by any particular theory, expanding the balloon against the filling structure (when filled), at a pressure greater than that in the filling structure, can result in increased pressure on the thrombus, portions of the aneurysm wall or both. This increased pressure, may be an effective amount of pressure or further increase the effects of the effective amount of pressure already applied to a thrombus.

The duration of application of the effective amount of pressure may vary. In an exemplary embodiment, the effective amount of pressure is maintained for at least 30 seconds, and preferably at least one minute. In another exemplary embodiment, the effective amount of pressure is maintained between about 1 to 10 minutes. Of course, the effective amount of pressure can be related to the pressure used to fill the filling structure as well as the expansion balloon. Therefore, in an exemplary embodiment, the expansion balloon is maintained at a pressure for a duration sufficient to produce an effective amount of pressure on a thrombus, aneurysm wall or a combination thereof.

The effective amount of pressure on a thrombus or aneurysm wall may be constant, cycled or both. In an exemplary embodiment, the pressure in the filling structure, in the expansion balloon, on the thrombus/aneurysm wall, or a combination thereof, may be constant for a period of time sufficient to achieve the desired benefits creating an effective amount of pressure on the thrombus/aneurysm wall to mitigate the effects of PIS. In an exemplary embodiment, the pressure in the filling structure, in the expansion balloon, on the thrombus/aneurysm wall, or a combination thereof is cycled between at least two different pressure values. The duration of each cycle or all cycles combined may be for a period of time sufficient to produce an effective amount of pressure on the thrombus/aneurysm wall to bring about the desired benefits such as mitigating the effects of PIS. Moreover, the pressure may be cycled between two or more pressure values. In particular, the pressure cycles may include points where an effective amount of pressure is achieved on the thrombus/aneurysm wall and where effective amount of pressure is not present. In an exemplary embodiment, the expansion balloon pressure is cycled between the first pressure and the second pressure for at least one minute. Without being bound by any theory, the cyclic application of an effective amount of pressure may be more efficient, for example, in displacing biological fluid from a thrombus. Moreover, in an exemplary embodiment, at least two cycles of application of effective amount of pressure is applied. In another exemplary embodiment, 2-100 cycles are applied.

In the exemplary embodiments, the application of an effective amount of pressure may vary based on the first or second filing agent. For instance, and again without being bound by any theory, when the saline solution is used for the first filling agent, the mechanical properties of the filling structure is expected to stay fairly constant during the period it remains filled. With a curable polymer used as the second filling agent, the mechanical properties of the filled filling structure may change as the polymer cures. Thus, in an exemplary embodiment, the pressure used to expand the expansion balloon against the filling structure is varied based on the changing physical properties of the filling bag. For instance, the pressure of the balloon may be rapidly or gradually increased as the polymer cures. In the alternative, the pressure of the balloon may be rapidly or gradually decreased as the polymer cures. Relatedly, the choice of the filing agent may be considered for optimizing the effective amount of pressure produced by filling the expansion balloon. In an exemplary embodiment, the polymer(s) used as the second filling agent may have a slow cure time to permit a longer duration of pressure application before the polymer.

In another exemplary embodiment, the polymer(s) used as the filing agent may have a rapid cure time when it is desirable to apply the effective amount of pressure when the polymer has solidified.

In order to further optimize the exemplary methods, one or more pressure sensors may be used. In an exemplary embodiment, the pressure profile in the aneurysm to be treated is measured prior to, or after, placement of the aneurysm. This data may inform the choice of filling agents, modes of pressure applied to the thrombus or aneurysm wall, among other things. In an exemplary embodiment, the pressure of the filling structure, expansion balloon or other regions in the aneurysmal space is monitored during the procedure to ensure the effective amount of pressure obtained. In some instances, based on the measured pressure in the aneurysmal space, the first pressure, second pressure, or both is adjusted to exceed the pressure in the aneurysm.

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent systems and methods within the scope of the present technology, in addition to those enumerated herein, will be apparent to those skilled in the art from the foregoing descriptions. Such modifications and variations are intended to fall within the scope of the present technology. It is to be understood that this present technology is not limited to particular systems and methods systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 agents refers to groups having 1, 2, or 3 agents. Similarly, a group having 1-5 agents refers to groups having 1, 2, 3, 4, or 5 agents, and so forth.

All patents, patent applications, provisional applications, and publications referred to or cited herein are incorporated by reference in their entirety, including all figures and tables, to the extent they are not inconsistent with the explicit teachings of this specification.

What is claimed is:

1. A method of treating an aortic aneurysm of a patient with an endovascular graft system and mitigating post implant syndrome inflammation resulting therefrom, comprising:
    placing at least one prosthesis in an aortic aneurysmal space, said prosthesis comprising a stent-graft and a double-walled filling structure, wherein the filling structure comprises an outer wall, an inner wall, and a fillable space between the outer wall and the inner wall;
    radially expanding the stent-graft with an expansion balloon at a first pressure of at least about 180 mm Hg;
    filling the filling structure with a first filling agent such that the filling structure expands and contacts a thrombus disposed in the aneurysmal space;
    removing the first filling agent from filling structure;
    filling the filling structure with a second filling agent such that the filling structure expands and contacts the thrombus;
    radially expanding the stent-graft with an expansion balloon at a second pressure thereby causing the filling structure with the second filling agent to place an effective amount of pressure on the thrombus;
    wherein the effective amount of pressure placed on the thrombus mitigates the effects of post implant syndrome associated with the prosthesis by reducing inflammation in the aneurysm.

2. The method of claim 1, further comprising the step of introducing the first filling agent into the fillable space, prior to radially expanding the stent-graft, such that the filling structure expands and contacts the thrombus disposed in the aortic aneurysmal space.

3. The method of claim 2, comprising radially expanding the stent-graft with an expansion balloon at the second pressure thereby causing the filling structure with the first filling agent to place an effective amount of pressure between about 190 mm Hg and about 300 mm Hg, on the thrombus, wherein said second pressure is greater than the first pressure.

4. The method of claim 1, wherein the expansion balloon is maintained in an expanded state at the first pressure for at least 30 seconds.

5. The method of claim 1, wherein the expansion balloon is maintained in an expanded state at the second pressure for at least 30 seconds.

6. The method of claim 1, wherein the expansion balloon is maintained in an expanded state at the first pressure, second pressure or both for about 1 minute to about 10 minutes.

7. The method of claim 1, wherein the pressure of the expansion balloon is cycled between the first pressure and the second pressure for at least 30 seconds.

8. The method of claim 3, wherein pressure of the expansion balloon is cycled between the first pressure and the second pressure for at least one minute.

9. The method of claim 1, further comprising measuring, with at least one sensor, the pressure profile of the aneurysm to be treated before placement of the prosthesis.

10. The method of claim 1, further comprising measuring, with at least one sensor, the pressure profile of the aneurysm to be treated after placing the prosthesis.

11. The method of claim 1, further comprising measuring, with at least one sensor, the pressure profile of the aortic aneurysm to be treated and adjusting the first pressure, second pressure, or both to exceed a maximum pressure measured inside the aneurysm.

12. The method of claim 1, wherein the filling structure comprises a channel which allows biological fluid from the thrombus or aneurysm wall to escape distally.

13. The method of claim 1, further comprising mechanically aspirating the thrombus in the aortic aneurysmal space.

14. The method of claim 1, further comprising delivering an agent that promotes maturation of thrombus.

15. The method of claim 1, comprising placing an effective amount of pressure between about 190 mm Hg and about 300 mm Hg on the thrombus to displace biological fluid from the thrombus or aneurysm wall.

16. The method of claim 15, wherein the biological fluid comprises pro-inflammatory agents.

17. The method of claim 15, further comprising placing an effective amount of pressure on the thrombus or aneurysm wall to promote biological remodeling in the aortic aneurysmal space.

18. The method of claim 17, wherein the biological remodeling comprises producing new fluid pathways between the aortic aneurysm space and a circulatory system of the patient.

19. The method of claim 17, wherein the biological remodeling comprises forming new vasculature.

20. The method of claim 1, further comprising anchoring or sealing the prosthesis proximally and distally.

21. The method of claim 1, wherein the outer surface of the outer wall of the filling structure comprises a therapeutic agent.

22. The method of claim 1, further comprising introducing a therapeutic agent into the aortic aneurysmal space before filling the filling structure.

* * * * *